(12) United States Patent
Betts et al.

(10) Patent No.: US 7,220,755 B2
(45) Date of Patent: May 22, 2007

(54) 42-O-ALKOXYALKYL RAPAMYCIN DERIVATIVES AND COMPOSITIONS COMPRISING SAME

(75) Inventors: Ronald E. Betts, La Jolla, CA (US);
Douglas R. Savage, Del Mar, CA (US);
John E. Shulze, Rancho Santa Margarita, CA (US)

(73) Assignee: Biosensors International Group, Ltd., Hamilton HMEX (BM)

(*) Notice: Subject to any disclaimer, the term of this patent is extended or adjusted under 35 U.S.C. 154(b) by 181 days.

(21) Appl. No.: 10/706,055

(22) Filed: Nov. 12, 2003

(65) Prior Publication Data

US 2005/0101624 A1    May 12, 2005

(51) Int. Cl.
*C07D 498/18* (2006.01)
*A61K 31/435* (2006.01)
*A61P 37/00* (2006.01)

(52) U.S. Cl. ........................ 514/291; 540/456
(58) Field of Classification Search ........... 540/456; 514/291
See application file for complete search history.

(56) References Cited

U.S. PATENT DOCUMENTS

| | | | |
|---|---|---|---|
| 4,650,803 A | 3/1987 | Stella et al. | |
| 5,120,842 A | 6/1992 | Failli et al. | |
| 5,151,413 A | 9/1992 | Caufield et al. | |
| 5,258,389 A | 11/1993 | Goulet et al. | |
| 5,378,836 A * | 1/1995 | Kao et al. | 540/456 |
| 5,665,772 A | 9/1997 | Cottens et al. | |
| 5,912,253 A * | 6/1999 | Cottens et al. | 514/291 |
| 5,985,890 A | 11/1999 | Cottens et al. | |
| 6,384,046 B1 | 5/2002 | Schuler et al. | |
| 6,440,990 B1 | 8/2002 | Cottens et al. | |
| 6,585,764 B2 | 7/2003 | Wright et al. | |
| 2002/0127248 A1 | 9/2002 | Schuler et al. | |

FOREIGN PATENT DOCUMENTS

| | | |
|---|---|---|
| EP | 0 867 438 A1 | 9/1998 |
| EP | 0 663 916 B1 | 11/1998 |
| WO | WO 95/16691 A1 | 6/1995 |
| WO | WO 97/35575 | 10/1997 |
| WO | WO 01/14387  * | 3/2001 |
| WO | WO 01/97809 A2 | 12/2001 |
| WO | WO 03/90684 A2 | 11/2003 |

* cited by examiner

*Primary Examiner*—Bruck Kifle
(74) *Attorney, Agent, or Firm*—Perkins Coie LLP

(57) ABSTRACT

42-O-alkoxyalkyl derivatives of rapamycin having biological activity are described. Compositions and delivery devices comprising the 42-O-alkoxyalkyl rapamycin derivatives are also disclosed.

12 Claims, 9 Drawing Sheets

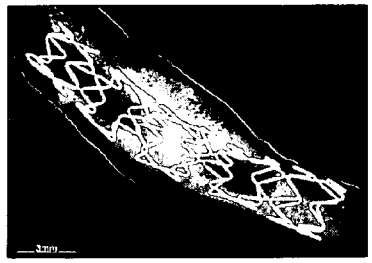 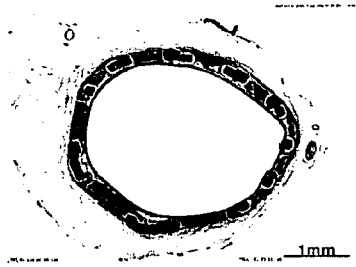 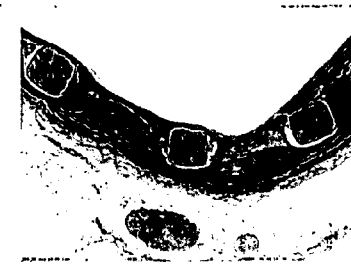
Fig. 5A        Fig. 5B        Fig. 5C
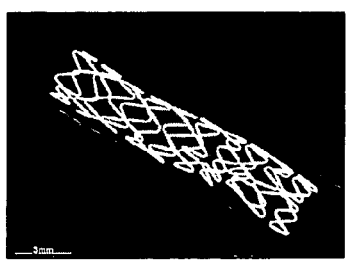 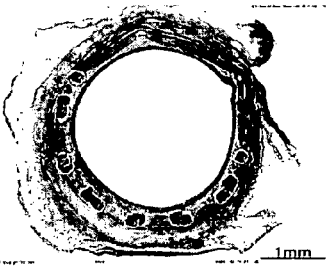 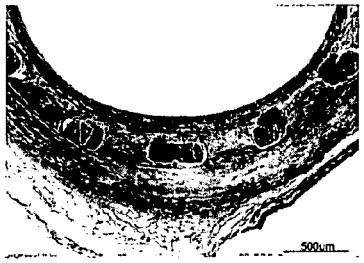
Fig. 5D        Fig. 5E        Fig. 5F
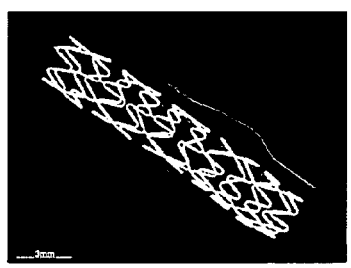  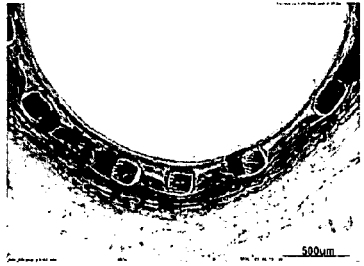
Fig. 5G        Fig. 5H        Fig. 5I

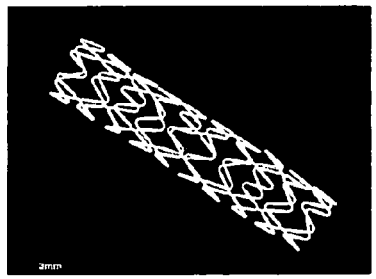 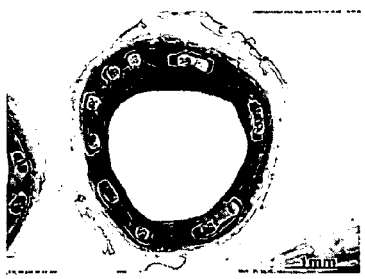 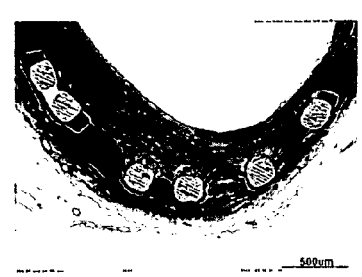
Fig. 7A    Fig. 7B    Fig. 7C
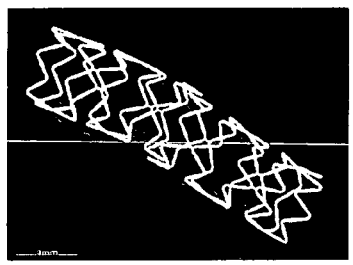 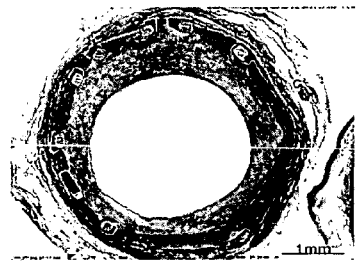 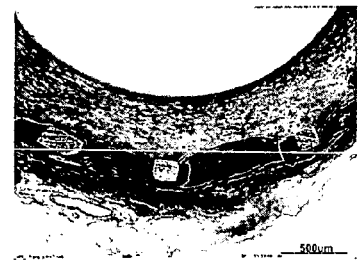
Fig. 8A    Fig. 8B    Fig. 8C
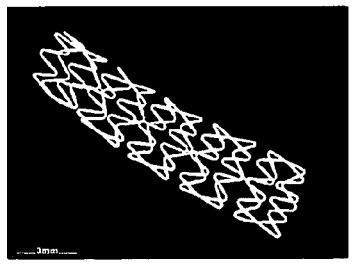 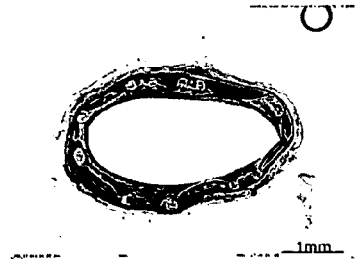 
Fig. 9A    Fig. 9B    Fig. 9C

42-O-ALKOXYALKYL RAPAMYCIN DERIVATIVES AND COMPOSITIONS COMPRISING SAME

FIELD OF THE INVENTION

The present invention relates to 42-O-alkoxyalkyl derivatives of rapamycin and to compositions comprising 42-O-alkoxyalkyl rapamycin derivatives.

BACKGROUND OF THE INVENTION

Rapamycin is a macrocyclic triene compound that was initially extracted from a streptomycete (*Streptomyces hygroscopicus*) isolated from a soil sample from Easter Island (Vezina et al., *J. Antibiot.* 28:721 (1975); U.S. Pat. Nos. 3,929,992; 3,993,749). Rapamycin has the structure depicted in Formula I:

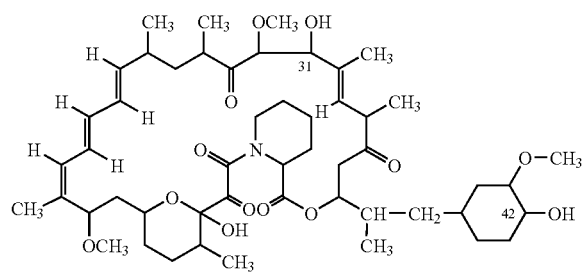

Originally described for use as an antifungal agent (U.S. Pat. No. 3,929,992), it has subsequently found to be an effective agent for other conditions and disorders, including use in the treatment of cancer and tumors (U.S. Pat. No. 4,885,171), use for the prevention of experimental immunopathies (experimental allergic encephalitis and adjuvant arthritis; Martel, R., *Can. J. Physiol.*, 55:48 (1977)), inhibition of transplant rejection (U.S. Pat. No. 5,100,899), and inhibition of smooth muscle cell proliferation (Morris, R., *J. Heart Lung Transplant*, 11 (pt. 2) (1992)).

The numbering convention for rapamycin has been recently changed, and under the revised Chemical Abstracts nomenclature, what was formerly the 40-position is now the 42-position and the former 28-position is now the 31-position.

The utility of the compound as a pharmaceutical drug has been restricted by its very low and variable bioavailability and its high toxicity. Also, rapamycin is only very slightly soluble in water, i.e., 20 micrograms per milliliter, making it difficult to formulate into stable compositions suitable for in vivo delivery. To overcome these problems, prodrugs and derivatives of the compound have been synthesized. Water soluble prodrugs prepared by derivatizing rapamycin positions 31 and 42 (formerly positions 28 and 40) of the rapamycin structure to form glycinate, propionate, and pyrrolidino butyrate prodrugs have been described (U.S. Pat. No. 4,650,803). The numerous derivatives of rapamycin described in the art include monoacyl and diacyl derivatives (U.S. Pat. No. 4,316,885), acetal derivatives (U.S. Pat. No. 5,151,413), silyl ethers (U.S. Pat. No. 5,120,842), hydroxyesters (U.S. Pat. No. 5,362,718), as well as alkyl, aryl, alkenyl, and alkynyl derivatives (U.S. Pat. Nos. 5,665,772; 5,258,389; 6,384,046; WO 97/35575).

One of the shortcomings of many of the prodrugs and derivatives of rapamycin is the complicated synthesis involved in preparing the prodrug or derivative, where additional synthetic steps are required to protect and deprotect certain positions. Also, care must be taken in designing prodrugs and derivatives to preserve activity of the compound and to sterically hinder positions necessary for protein binding or other cellular interactions. Derivatives having a shorter overall chain length and/or overall steric bulk (volume) in the chemical moiety attached to the compound are less likely to produce steric hindrance of binding sites. It would be desirable to design a derivative that has a shorter chain length or smaller size in the attached moiety.

One of the recent therapeutic uses of rapamycin and its derivatives has been treatment of restenosis. Restenosis after percutaneous transluminal coronary angioplasty (PTCA) remains one of its major limitations (Hamon, M. et al., *Drug Therapy*, 4:291–301 (1998)). The occurrence of restenosis after initial PTCA is between 30 and 50%, despite initial success (Bauters, C. et al., *Am. Coll. Cardiol.*, 20:845–848 (1992); Bauters C. et al., *Eur. Heart J.*, 16:33–48 (1995)). Restenosis after PTCA is thought to be a two component process of both intimal hyperplasia and vascular remodeling, the former coming initially, the latter occurring later in the process (Hoffman, R. et al., *Circulation*, 94:1247–1254 (1996); Oesterle, S. et al., *Am. Heart J.*, 136:578–599 (1998)).

One strategy to eliminate or reduce restenosis is to limit the process of vascular remodeling. This can be accomplished by placing a stent in the lumen of the vessel after PTCA. Coronary stents are small metal tubular implants that are being extensively used to prevent acute reclosure or collapse of vessels following angioplasty. Currently, stents are routinely placed in 70 to 80% of all interventional cases.

In many cases this strategy works, however, the problem of restenosis is yet to be fully understood or conquered (Hamon, M. et al., *Drug Therapy*, 4:291–301 (1998); Oesterle, S. et al., *Am. Heart J.*, 136:578–599 (1998)) The injury caused by angioplasty and stent placement often causes excessive healing response, including thrombosis and rapid cell proliferation inside the stent, leading to eventual reclosure of the vascular channel. There remains a need to solve the eventual renarrowing of the lumen inside the stent (i.e. restenosis) after angioplasty and stent placement experienced by many patients.

SUMMARY OF THE INVENTION

Accordingly, it is an object of the invention to provide a compound for treatment of conditions responsive to treatment by rapamycin. More specifically, it is an object of the invention to provide an ether-like derivative of rapamycin that possess immunosuppressive, antifungal, anti-tumor, and/or anti-inflammatory activity in vivo and therefore useful in the treatment of transplantation rejection, infectious diseases, autoimmune diseases, and conditions characterized by excessive cell proliferation.

It is another object of the invention to provide a composition comprising a 42-O-alkoxyalkyl derivative of rapamycin.

It is still another objective of the invention to provide derivatives of rapamycin that are synthetically prepared with ease relative to other rapamycin derivatives.

It is yet another objective of the invention to provide a stent capable of eluting 42-O-alkoxyalkyl derivative of rapamycin.

In one aspect, the invention includes a compound of the form:

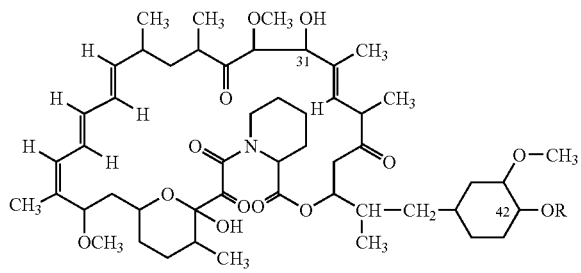

wherein R is $R^a$—O—$R^b$, where $R^a$ is $C_{2-6}$ alkylene and $R^b$ is $C_{1-5}$ alkyl, and where the number of carbon atoms in the sum of $R^a$ and $R^b$ is 7 or fewer. In various embodiments, R is of the form —$(CH_2)_n$—O—$(CH_2)_m$H, where n is from 2 to 6 and m is from 1 to 5; n is 2–5 and m is 1–4; n is 2 and m is 1 or 2; n is 2 and m is 1 ; and n is 2 and m is 2. In other embodiments, the number of carbon atoms in the sum of $R^a$ and $R^b$ is 6 or fewer, preferably 5 or fewer, more preferably 4 or fewer.

In another aspect, the invention includes a composition comprising a compound as described above, together with a carrier. In various embodiments, the carrier is a pharmaceutical preparation having the form of an ointment or a gel, polymer microparticles, or a pharmaceutical preparation having the form of a liquid.

In a preferred embodiment, the carrier is a stent. The stent can be formed of metal or polymer, including biodegradable polymers. When the carrier is a stent, in one embodiment the drug compound can be carried directly on the surface of the stent. Alternatively, the compound is carried in a polymer layer in contact with the stent.

In another aspect, the invention includes a stent for use in treating restenosis. The stent is comprised of an expandable stent body; and carried on the stent body for release therefrom at a controlled rate, is a compound having the form given above. The stent body can be formed of metal or polymer, including a biodegradable polymer.

In one embodiment, the stent further includes a polymer layer in contact with the stent body and the compound is incorporated into the polymer layer. The polymer layer can be comprised of a biodegradable polymer or a non-biodegradable polymer.

In another embodiment, the stent includes a polymer underlayer disposed between the stent body and the compound or polymer layer.

In other embodiment, the surface of the stent body is treated to enhance adhesion of the drug compound, relative to a stent surface with no treatment. For example, in one embodiment, the stent surface is treated with a nitric acid solution. In other alternative embodiment, the stent surface is treated by a process such as sand blasting, laser etching, or chemical etching.

In other embodiment, the compound is applied to the stent surface from a solution of the compound in an organic solvent.

The stent can also include a membrane applied over the compound to control bioavailability of the compound. For example, a membrane formed of a polymer material and placed over the drug-coated stent is contemplated to control the release rate of the compound.

In another embodiment, the stent includes a polymer underlayer in contact with the stent surface, and the compound/polymer film is in contact with the polymer underlayer. That is, the underlayer is disposed between the stent body and the drug-laden polymer layer. Exemplary polymer underlayers are polytetrafluoroethylene (Teflon) and poly(dichloro-para-xylylene) (Parylene).

In one embodiment, the compound is applied to the stent body in the form of a solution of the compound in an organic solvent. The solution is applied to the stent by a technique selected from brushing, spraying, dipping, and flowing. In a preferred embodiment, application of the compound is done in such a way as to form a glassy layer of compound on the stent surface. Solutions comprised of between about 2 and 60% by weight compound, remainder solvent, are preferred. An exemplary organic solvent is ethyl acetate.

In yet another aspect, the invention includes a method of treating a condition responsive to treatment by rapamycin, by administering a compound having the form described above. The compound can be administered in the form of a carrier, such as those described above.

In another aspect, the invention includes a method of treating restenosis, comprising providing a stent, as described above.

These and other objects and features of the invention will be more fully appreciated when the following detailed description of the invention is read in conjunction with the accompanying drawings.

BRIEF DESCRIPTION OF THE DRAWINGS

FIGS. 5A–5I are computer-generated photomicrographs of histology slides for a pig implanted with three 42-O-(2-ethoxyethyl) rapamycin eluting stents, the stents placed in the left anterior descending artery (FIGS. 5A–5C), the left circumflex artery (FIGS. 5D–5F), and the right coronary artery (FIGS. 5G–5I);

FIGS. 7A–7C show the right coronary artery of a control animal 30 days after implant of a bare, metal stent, where FIG. 7A shows an image of the stent in place in the artery and FIGS. 7B–7C show cross-sectional views of the stent at two different magnifications;

FIGS. 8A–8C show the left anterior descending artery of a control animal 30 days after implant of a bare, metal stent, where FIG. 8A shows an image of the stent in place in the artery and FIGS. 8B–8C show cross-sectional views of the stent at two different magnifications;

FIGS. 9A–9C show the left circumflex artery of a control animal 30 days after implant of a bare, metal stent, where FIG. 9A shows an image of the stent in place in the artery and FIGS. 9B–9C show cross-sectional views of the stent at two different magnifications;

DETAILED DESCRIPTION OF THE INVENTION

I. Definitions

Figure 1:
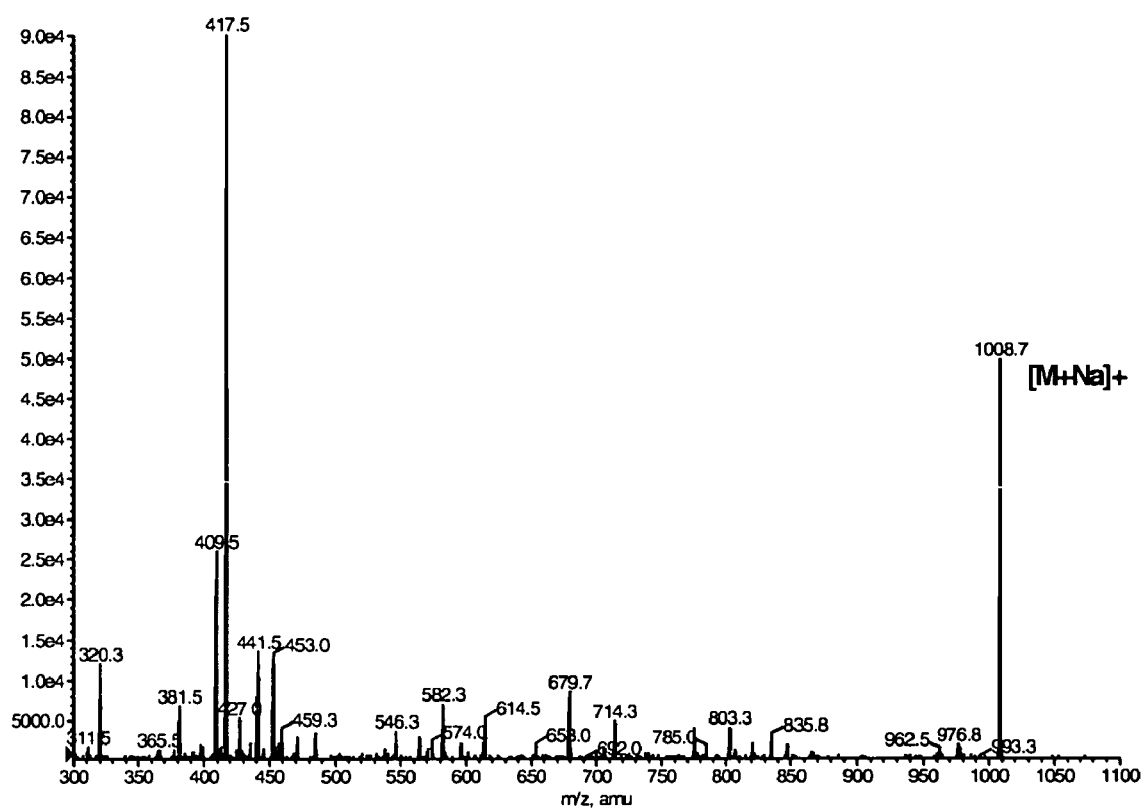
FIG. 1 shows a representative MS fragmentation pattern of a 42-O-alkoxyalkyl rapamycin derivative, 42-O-(2-ethoxyethyl) rapamycin.

"Rapamycin" as used herein intends a compound of the structure:

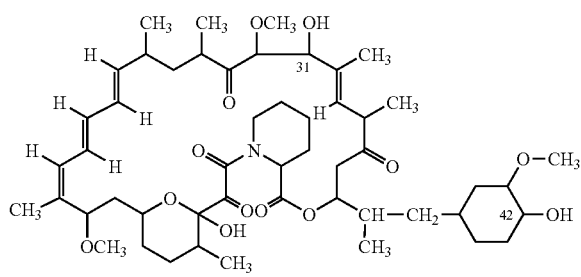

This compound is also known in the art as 'sirolimus'.

A "42-O-alkoxyalkyl rapamycin derivative" refers to a compound where the hydroxyl group at carbon number 42 in the rapamycin compound is modified with a moiety of the form $(CH_2)_n$—O—$(CH_2)_m$H, where n is two (2) or more and m is one (1) or more. Recently, the numbering convention for rapamycin has changed, and under the revised Chemical Abstracts nomenclature, what was formerly the 40-position is now the 42-position.

"Everolimus" intends a compound of the structure:

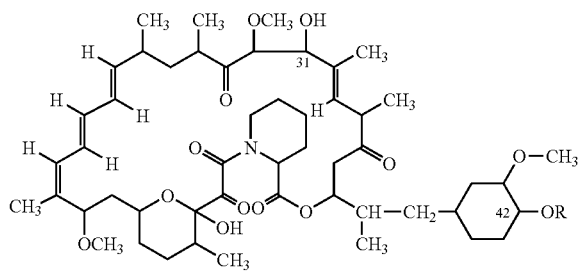

where R is $CH_2CH_2OH$ (hydroxy ethyl).

The compound referred to herein as "42-O-hydroxy heptyl rapamycin" refers to the structure shown for everolimus where the R group is of the form $(CH_2)_7OH$.

An "efficacious amount" or an "effective amount" intends a dosage sufficient to provide treatment for the disorder or disease state being treated. This will vary depending on the patient, the disease, and the treatment being effected, but is readily determined using clinical markers particular to the disorder or disease of concern. For example, a cross-sectional area measurement of the amount of new cells (i.e. tissue) growth inside a stent after implantation and injury of the vessel wall by overexpansion of the stent with a balloon catheter provides a clinical marker for restenosis. A reduction or stabilization of tissue volume after application of a dosage of active drug at a tumor site provides a clinical marker for tumor treatment. A clinical marker relating to organ transplant or vascular graft surgery would be to monitor organ function or to monitor continued patency (i.e. freedom from reocclusion or renarrowing) of transplant allografts. For skin wounds, a clinical marker would be to watch for a change in inflammation markers of redness, granuloma formation, or fibrosis. For an enlarged prostate, a clinical marker would be to monitor for any reduction in recurrence of ureter blockage.

II. 42-O-alkoxyalkyl Rapamycin Derivative Compounds

In one aspect, the invention provides rapamycin derivatives, specifically 42-O-(alkoxyalkyl) rapamycin derivatives of the form:

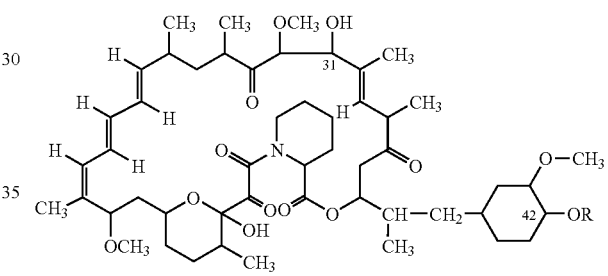

where R is $R^a$—O—$R^b$, where $R^a$ is $C_{2-6}$ alkylene and $R^b$ is $C_{1-5}$ alkyl, and where the number of carbon atoms in the sum of $R^a$ and $R^b$ is 7 or fewer. As used herein, "alkylene" refers to a divalent alkyl group, e.g. —$CH_2CH_2$— (ethylene). Preferably, $R^a$ is $C_{2-5}$ alkylene and $R^b$ is $C_{1-4}$ alkyl, and the sum of the carbon atoms in $R^a$ and $R^b$ is 7 or fewer, preferably 6 or fewer, more preferably 5 or fewer. In $R^a$ and $R^b$, alkylene or alkyl groups having three or more carbons may be either linear or branched or cyclic. When each of $R^a$ and $R^b$ is linear, R may be represented by —$(CH_2)_n$—O—$(CH_2)_m$H, where n is from 2 to 6 and m is from 1 to 5.

In selected embodiments, n is 2–4 and m is 1–4. Preferably, m is 1 or 2. In further selected embodiments, n is 2 (i.e., $R^a$ is ethylene) and m is 1 or 2 (i.e., $R^b$ is methyl or ethyl). In a particularly preferred embodiment, each of n and m is 2 (i.e., $R^a$ is ethylene and $R^b$ is ethyl), to give the compound 42-O-(ethoxyethyl) rapamycin.

The rapamycin 42-O-(alkoxyalkyl) derivatives of the invention may be prepared by reaction of the 42-hydroxyl group of rapamycin with a compound of the form L—$R^a$—O—$R^b$, where $R^a$ and $R^b$ are as defined above and L is a leaving group. Suitable leaving groups include, for example, halogens, such as bromo or iodo, and sulfonates, such as tosylate, mesylate, or trifluoromethane sulfonate (triflate). The derivative is formed by displacement of the leaving group by the 42-hydroxyl group of rapamycin, as illustrated in Example 1. A representative product ion scan of 42-O-

(2-ethoxyethyl) rapamycin obtained using tandem mass spectrometry (Sciex API4000) is shown in FIG. 1.

Compounds of the form L—$R^a$—O—$R^b$ are readily prepared from the corresponding alkoxy alcohols HO—$R^a$—O—$R^b$, by reaction with, for example, trifluoromethylsulfonic (triflic) anhydride, generally in the presence of an amine catalyst such as lutidine, as described in Example 1 below.

Many such alkoxy alcohols are commercially available. For example, the compounds 2-ethoxy ethanol, 2-methoxy ethanol, 1-methoxy-2-propanol, 3-ethoxy-1-propanol, 2-isopropoxy ethanol, 1-methoxy-2-butanol, 3-methoxy-1-butanol, 2-propoxy ethanol, 2-butoxy ethanol, 3-methoxy-3-methyl-1-butanol, 3-propoxy propanol, 1-tert-butoxy-2-propanol, 3-butoxy propanol, and propylene glycol butyl ether are all available from Aldrich Corporation. With respect to selected embodiments above, the subject compounds in which n is 2 (i.e., $R^a$ is ethylene) and m is 1–2 (i.e., $R^b$ is methyl or ethyl) can be prepared using 2-methoxy ethanol and 2-ethoxy ethanol, respectively. Preparation of 42-O-(2-methoxyethyl) rapamycin is described in Example 2, and preparation of 42-O-(2-ethoxyethyl) rapamycin is described in Example 1.

Alkoxy alcohols HO—$R^a$—O—$R^b$ are commercially available or can also be prepared from the corresponding diols HO—$R^a$—OH by etherification with $R^b$, preferably using a process which gives predominantly or exclusively a monoderivatized product. For example, Shanzer (Tet. Lett. 21(2), 221–2, 1980) describes a process for efficient monoalkylation of diols by reaction of a stannoxane intermediate, derived from the diol, with an alkyl halide. Martinelli et al., describe monotosylation of diols by reaction with α-toluenesulfonyl chloride and triethylamine in the presence of catalytic $Bu_2SnO$ (J. Am. Chem. Soc. 124(14): 3578–3585, 2002). The monotosylate could then be treated with an alkoxide to give the alkoxy alcohol. The cited procedures are most suitable for 1,2-diols; that is, where $R^a$ represents a two-carbon chain separating the hydroxyl groups (as in the preferred derivatives). A method for monoderivatization of longer diols is given by McDougal (J. Org. Chem., 51:3388 (1986)). A high yield of tert-butyldimethylsilyl monosilyated product (TBS—$OR^a$—OH) is obtained from symmetric diols. This protected product can then be activated with a suitable leaving group such as triflate by reaction with trifluoromethane sulfonic anhydride and a suitable base such as 2,6-lutidine. Reaction of the triflate product with the appropriate alcohol ($R^b$—OH) and 2,6-lutidine followed by hydrolysis of the silyl protecting group with acid will afford the alkoxy alcohol. In the case of non-symmetrical diols, the less hindered terminus will generally react preferentially. In any case, any bis-alkoxy side product (e.g. $R^bO$—$R^a$—$OR^b$) can easily be separated from the desired alkoxy alcohol (HO—$R^a$—$OR^b$) by standard purification procedures, such as chromatography.

Potency of 42-O-(2-ethoxyethyl) rapamycin was tested in vitro and compared to the potency of another rapamycin derivative, 42-O-hydroxy heptyl rapamycin, and to the potency of rapamycin. The testing procedure is described in Example 3 and the results are shown in FIG. 2.

Figure 2:
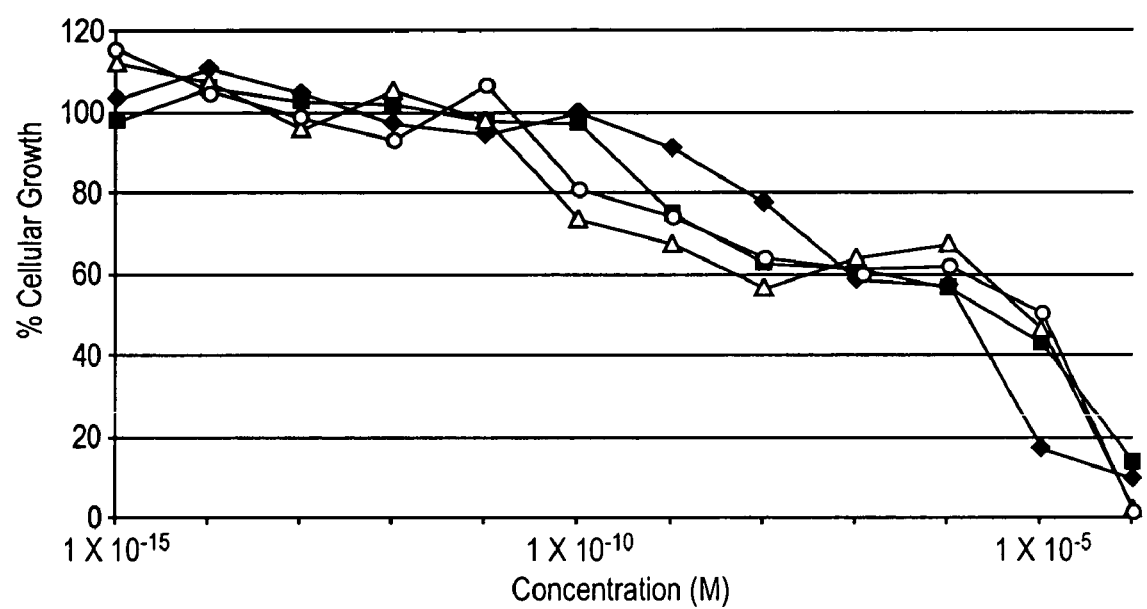
FIG. 2 is a plot showing cellular proliferation of human smooth muscle cells in vitro, expressed as the percentage of growth relative to control cells, as a function of molar drug concentration of 42-O-(2-ethoxyethyl) rapamycin (squares), rapamycin (triangles, circles), and 42-O-(hydroxy heptyl) rapamycin (diamonds)

42-O-(2-ethoxyethyl) rapamycin (squares) derivative effectively inhibited growth of smooth muscle cells over five orders of magnitude concentration, for both porcine and human cells, as seen in FIG. 2. It was also observed that 42-O-(2-ethoxyethyl) rapamycin inhibited cellular growth as effectively as 42-O-hydroxy heptyl rapamycin (diamonds) or rapamycin (triangles, circles).

III. Compositions Comprising a 42-O-Alkoxyalkyl Rapamycin Derivative

In another aspect, the invention includes a composition incorporating a 42-O-(alkoxyalkyl) rapamycin derivative compound. A wide variety of compositions and formulations are contemplated and several specific examples will be discussed in more detail below. In general, the composition serves as a sort of drug reservoir which contains and releases the compound after application or deposition of the composition at a target site.

A. Polymer Particles

An exemplary composition is a formulation of polymer particles that are suitable for placement in vivo via injection or via transport and deposition using a device, such as a catheter. The polymer particles can be microporous, macroporous, or non-porous and can be formed of a polymer that is capable of retaining the desired 42-O-alkoxyalkyl rapamycin derivative compound.

Porous polymer particles have interconnected pores which open to the particle surface for communication between the exterior of the particle and the internal pore spaces. Exemplary particles for formation of such macroporous reservoirs are described, for example, in U.S. Pat. No. 5,135,740, incorporated by reference herein. In brief, porous particles are formed, for example, by suspension polymerization in a liquid-liquid system. In general, a solution containing monomers and a polymerization catalyst is formed that is immiscible with water. An inert solvent miscible with the solution but immiscible with water is included in the solution. The solution is then suspended in an aqueous solution, which generally contains additives such as surfactants and dispersants to promote the suspension or emulsion. Once the suspension is established with discrete droplets of the desired size, polymerization is effected, typically by activating the reactants by either increased temperature or irradiation. Once polymerization is complete, the resulting solid particles are recovered from the suspension. The particles are solid, spherical, porous structures, the polymer having formed around the inert liquid, thereby forming the pore network. The inert solvent, which served as a porogen, or pore-forming agent, occupies the pores of the particles. The porogen is subsequently removed.

The macroporous particles can also be prepared by solvent evaporation, from either a biodegradable or a non-degradable polymer. For the solvent-evaporation process, the desired polymer is dissolved in an organic solvent and the solution is then poured over a layer of sodium chloride crystals of the desired particle size (Mooney, et al., J. Biomed. Mater. Res. 37:413–420, (1997)). The solvent is removed, generally by evaporation, and the resulting solid polymer is immersed in water to leach out the sodium chloride, yielding a porous polymer reservoir. Alternatively sodium chloride crystals can be dispersed in the polymer solution by stirring to obtain a uniform dispersion of the sodium chloride crystals. The dispersion is then extruded dropwise into a non-solvent for the polymer while stirring to precipitate the polymer droplets around the sodium chloride crystals. The solid polymer particles are collected by filtration or centrifugation and then immersed in water to leach out the sodium chloride, yielding a porous polymer reservoir. It will be appreciated that alternatives to sodium chloride include any non-toxic water soluble salt or low molecular weight water soluble polymer which can be leached out to produce the desired porosity.

The porous particles can be loaded with one or more drugs by including the compounds in the polymer during particle formation or by loading the particles post-particle formation. Post-particle loading can be done by, for example, dissolving the drug compound in a solvent that acts to solvate the drug but that is a nonsolvent for the polymer and mixing by stirring the particles and the drug solution. The solution of drug is absorbed by the particles to give a free flowing powder. The particles may then be treated for solvent removal, as needed.

Another exemplary polymer particle composition is non-porous particles, such as microcapsule and microparticles having the compound contained or dispersed therein. Both microcapsules and microparticles are well known in the pharmaceutical and drug delivery industries (see, for example, Baker, R. W., CONTROLLED RELEASE OF BIOLOGICALLY ACTIVE AGENTS, John Wiley & Sons, NY, 1987; Ranade V. and Hollinger, M., DRUG DELIVERY SYSTEMS, CRC Press, 1996). Microcapsules typically refer to a reservoir of active agent surrounded by a polymer membrane shell. A microparticle typically refers to a monolithic system where the therapeutic agent(s) is dispersed throughout the particle. There are, however, many formulations falling between these two definitions, such as agglomerates of microcapsules, and such formulations would also be suitable for use herein.

Microcapsules and microparticles can be prepared from biodegradable or non-biodegradable polymers. Microcapsules are readily formed by a number of methods, including coacervation, interfacial polymerization, solvent evaporation, and physical encapsulation methods (, Baker, R. W., CONTROLLED RELEASE OF BIOLOGICALLY ACTIVE AGENTS, John Wiley & Sons, NY, 1987). Microparticles are prepared by numerous techniques known in the art, one simple way being to merely grind a polymer film containing dispersed therapeutic agent into a suitable size. Spray drying particulate therapeutic agent from a polymer solution is another approach. Specific procedures for encapsulation of biologically active agents are disclosed in U.S. Pat. No. 4,675,189 and U.S. Patent Application No. 20010033868, which are incorporated by reference herein.

Polymers suitable for particle formation are numerous and varied; the general selection criterion being a polymer capable of carrying a 42-O-alkoxyalkyl rapamycin derivative compound. Exemplary polymers include, but are not limited to, poly(d, l-lactic acid), poly(l-lactic acid), poly(d-lactic acid), methacrylate polymers, such as polybutyl methacrylate and the like, ethylene vinyl alcohol (EVOH), $\epsilon$-caprolactone, glycolide, ethylvinyl hydroxylated acetate (EVA), polyvinyl alcohol (PVA), polyethylene oxides (PEO), polyester amides, and co-polymers thereof and mixtures thereof. These polymers all have a history of safe and low inflammatory use in the systemic circulation. Typically, between 20–70 weight percent of polymer will be combined with between 30–80 weight percent of the 42-O-hydroxy alkyl substituted rapamycin compound to form the polymer composition.

The particles, whether porous or non-porous, may vary widely in size, from about 0.1 micron to about 100 microns in diameter, preferably from about 0.5 microns to about 40 microns. The particles can be administered as neat particles, or can be formulated in a gel, paste, ointment, salve, or viscous liquid for application at the target site.

In another embodiment, polymer particles are admixed with the rapamycin derivative and the mixture is applied to the surface of a stent. The polymer particles in this embodiment serve to bind the drug into a coating material and to control the release rate of drug from the coating. Particles formed of waxes, lipids, short chain polymers, such as propane and butane, are suitable.

As exemplified by the polymer particles, the polymer composition of the invention is one capable of being dispensed or placed at the target site, for contact of the polymer composition with the tissue at the target site. Those of skill in the art will appreciate that polymer particles are merely one example of a composition that achieves contact with the target tissue. Polymers capable of carrying a load of a hydrophobic compound can be formulated into films, patches, pastes, salves, or gels, all of which can be placed or dispensed at the target site. For example, a simple polymer patch prepared from a polymer loaded with the 42-O-alkoxyalkyl rapamycin derivative compound can be placed on the surface of tissue in need of treatment. Such a tissue surface can be a vessel, an organ, a tumor, or an injured or wounded body surface.

B. Mucoadhesive Polymer Composition

In another embodiment, the composition is comprised of a polymer substrate having mucoadhesive properties, for placement adjacent mucosal tissue. Mucosal sites in the body include the cul-de-sac of the eye, buccal cavity, nose, rectum, vagina, periodontal pocket, intestines and colon. Mucoadhesive delivery systems exhibit adhesion to mucosal tissues for administration of the compound(s) contained within the mucoadhesive polymer.

A variety of polymeric compositions are used in mucosal delivery formulations. Of particular interest for use with the 42-O-alkoxyalkyl rapamycin derivative compounds are mucoadhesives having a combination of hydrophilic and hydrophobic properties. Adhesives which are a combination of pectin, gelatin, and sodium carboxymethyl cellulose in a tacky hydrocarbon polymer, for adhering to the oral mucosa, are exemplary. Other mucoadhesives that have hydrophilic and hydrophobic domains include, for example, copolymers of poly(methyl vinyl ether/maleic anhydride) and gelatin, dispersed in an ointment base, such as mineral oil containing dispersed polyethylene (U.S. Pat. No. 4,948,580). Another hydrophilic/hydrophobic system is described in U.S. Pat. No. 5,413,792 where a paste-like preparation of a polyorganosiloxane and a water soluble polymeric material is disclosed.

In the present invention, a polymer composition comprised of a mucoadhesive polymer substrate and a 42-O-alkoxyalkyl rapamycin derivative compound is contemplated. The mucoadhesive polymer composition is formulated into a delivery system suitable for placement adjacent a mucosal surface. The compound when placed adjacent the mucosal tissue elutes from the polymer composition into the tissue. The delivery system can take the form of a patch for placement on the surface of tissue to be treated. The tissue can be an organ, a vessel, a tumor, or any body surface needing treatment.

C. Conventional Drug Delivery Compositions: Liquid, Ointment, Gel, Patch

The 42-O-alkoxyalkyl derivative compounds, in other embodiments, are formulated into pharmaceutical preparations of solid, semisolid, or liquid form. Such preparations are well known in the art, where the active ingredient is mixed with an organic or inorganic carrier or excipient suitable for external, enteral, or parenteral administration. Carriers and excipients for preparation of tablets, pellets, capsules, suppositories, solutions, emulsions, suspensions, are well known and include, but are not limited to, water, glucose, lactose, gum acacia, gelatin, mannitol, starch, magnesium trisilicate, talc, keratin, colloidal silica, urea, and the like. Stabilizing agents and thickening agents may also be used.

Liquid formulations are comprised of one or more 42-O-alkoxyalkyl derivative compounds admixed with a liquid carrier or excipient. Such a formulation can include other components, such as stabilizers, as desired. When admixed with the carrier, the 42-O-alkoxyalkyl derivative compound may be present in a dissolved state or in a suspended state. Components, particularly organic solvents, to enhance solubility of the 42-O-alkoxyalkyl derivative compound can be added.

Preparation of gels or ointments is also contemplated. Thickening agents added to a liquid preparation containing a 42-O-alkoxyalkyl derivative compound is a simplified approach to gel preparation. Components to enhance transport of the active compound across skin, mucosa, and cell membranes in general, can be included in the gel or ointment.

The 42-O-alkoxyalkyl derivative compounds can also be formulated into topical patches for application to a body surface, including the skin and mucosal body surfaces. Preparation of such topical patches is well known in the drug delivery field.

D. Endovascular Stent

Another exemplary carrier for use in the composition of the present invention is a stent. Endovascular stents are typically cylindrically-shaped devices capable of radial expansion. When placed in a body lumen, a stent in its expanded condition exerts a radial pressure on the lumen wall to counter any tendency of the lumen to close. Stents have found a particular use in maintaining vessel patency following angioplasty, e.g., in preventing restenosis of the vessel. In this application, a stent is inserted into a damaged vessel by mounting the stent on a balloon catheter and advancing the catheter to the desired location in the patient's body, inflating the balloon to expand the stent, and then deflating the balloon and removing the catheter. The stent in its expanded condition in the vessel exerts a radial pressure on the vessel wall at the lesion site, to counter any tendency of the vessel to close. "Self-expanding" stents are also known, made from spring material, mesh tubes, or shape-memory alloys, these devices are typically mounted on a catheter shaft surrounded by a sheath that constrains the expansion of the spring elements of the stent until the stent is positioned at the lesion site. Retraction of the sheath portion allows the stent to expand and contact the vessel lumen.

1. Stent Geometry

In this embodiment of the invention, the stent carries one or more 42-O-alkoxyalkyl rapamycin derivative compounds. The compound can be carried on the external surface of the stent, for direct contact with a lumen wall when the stent is deployed in a lumen, on the internal stent surface, or on both the internal and external stent surfaces. The compound(s) could also be carried on only select portions of the stent surface to obtain more localized therapeutic effects (see for example co-owned U.S. application Ser. No. 10/133,814 and PCT application no. PCT/US03/12750, which are incorporated herein by reference). The compound can be carried directly on the stent surface or can be incorporated into a polymer that is carried by the stent, as will be described below.

Numerous stent geometries and configurations are known in the art, and any of the geometries are suitable for use herein. The basic requirements of the stent geometry are (1) that it be expandable upon deployment at a vascular injury site, and (2) that it is suitable for receiving a coating of drug, or for carrying a drug-containing coating, on its surface, for delivering drug into the lumen in which the stent is placed. Preferably, the stent body also has a lattice or mesh structure, allowing viable endothelial cells in the stent "windows" to grow over and encapsulate the stent struts which are supporting the vessel lumen. The stent body can be formed of metal or polymer, including biodegradable polymers.

Figure 3A:
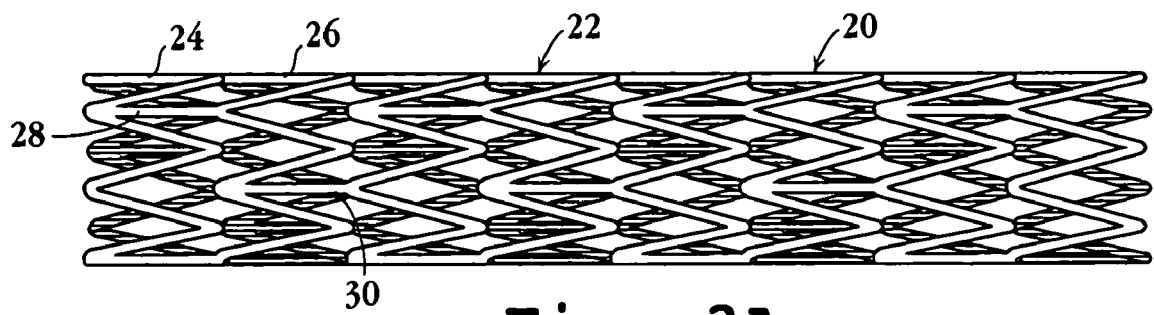
FIGS. 3A–3C illustrate an endovascular stent having a metal-filament body, and formed in accordance with one embodiment of the present invention, showing the stent in its contracted (FIG. 3A) and expanded (FIG. 3B, FIG. 3C) conditions in side view (FIG. 3B) and cross-sectional view (FIG. 3C)
Figure 3B:
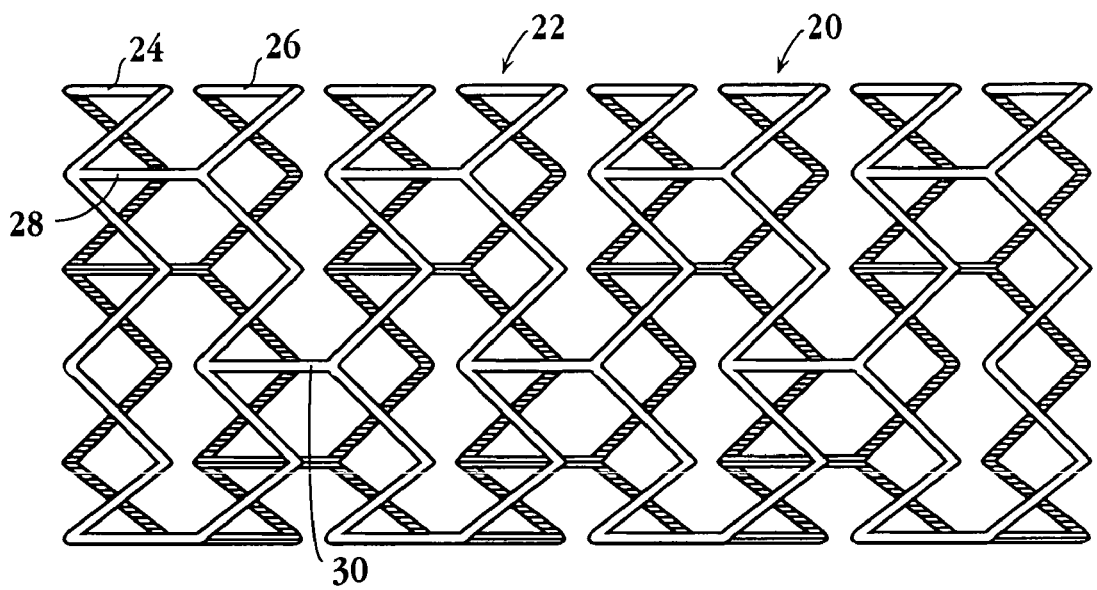
Figure 3C:
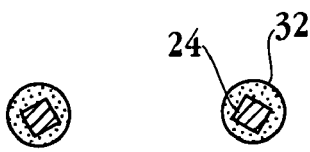
Figure 3C:
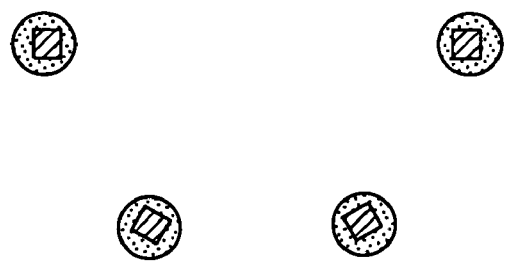
Figure 4:
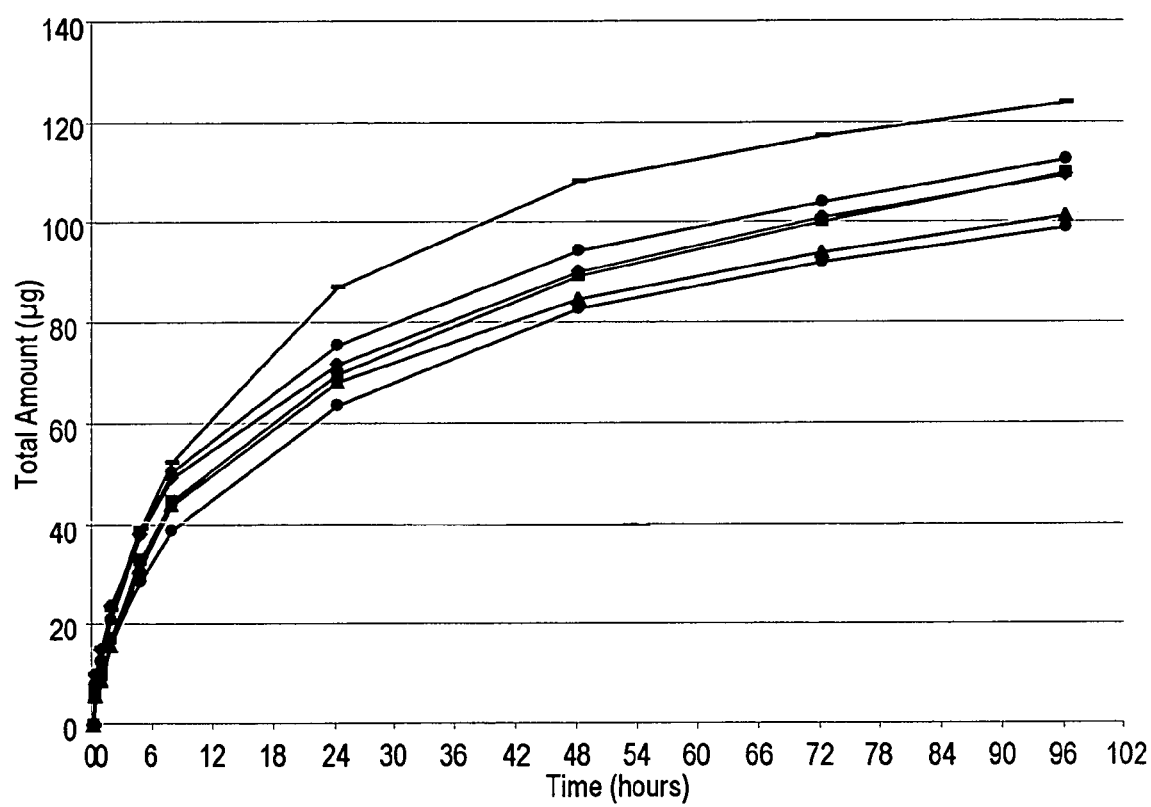
FIG. 4 shows the in vitro release rate of drug, in μg, into an ethanol-water release medium as a function of time, in hours, from six stents, each carrying a poly-dl-lactic acid layer loaded with (42-O-(2-ethoxyethyl) rapamycin.

One preferred stent configuration is shown in FIGS. 3 and 4 where an endovascular stent suitable for carrying a 42-O-alkoxyalkyl derivative is illustrated. Shown in FIGS. 3A–3B is a stent 20 in a contracted state (FIG. 3A) and an expanded state (FIG. 3B). The stent includes a structural member or body 22 having an outer surface for holding, directly or indirectly, and releasing the 42-O-alkoxyalkyl rapamycin derivative compound, as will be described further below. The stent body is formed of a plurality of linked tubular members, such as members 24, 26. Each member is comprised of a filament that has an expandable zig-zag, sawtooth, or sinusoidal wave configuration. The members are linked by axial links, such as links 28, 30 joining the peaks and troughs of adjacent members. This construction allows the stent to be expanded from a contracted condition, shown in FIG. 3A, to an expanded condition, shown in FIG. 3B, with little or no change in the length of the stent. At the same time, the relatively infrequent links between peaks and troughs of adjacent tubular members allows the stent to accommodate axial bending and flexing. This feature may be particularly important when the stent is being delivered to a vascular site in its contracted state, as in or on a catheter. The stent has a typical contracted-state diameter (FIG. 3A) of between 0.5–2 mm, more preferably 0.71 to 1.65 mm, and a length of between 5–100 mm. In its expanded state, shown in FIG. 3B, the stent diameter is at least twice and up to 8–9 times that of the stent in its contracted state. Thus, a stent with a contracted diameter of between 0.7 to 1.5 mm may expand radially to a selected expanded state of between 2–8 mm or more.

FIG. 3C shows the stent of FIGS. 3A–3B in cross-sectional view. The view is taken through stent tubular member 24, with adjacent tubular members visible. The stent body, and more specifically each tubular member, is coated with drug or with a polymer-drug composition, for release of drug from the stent at a target site. As will be more fully described below, the drug or drug-polymer layer is applied to the external surface of the stent, and can be deposited to achieve a uniform deposition thickness or a non-uniform deposition thickness. FIG. 3C illustrates the embodiment where the drug-polymer layer 32 is applied non-uniformly so that the external stent surface has a thicker drug or drug-polymer coating than the internal stent surface.

2. Drug Coating

The stent serves as a carrier for a 42-O-alkoxyalkyl derivative compound, which, as noted above, can be coated directly onto the stent or can be incorporated into a polymer matrix that is carried on the stent. Whether the drug is applied directly to the stent surface or incorporated into a polymer film on the stent surface, it is desirable that the 42-O-alkoxyalkyl rapamycin derivative compound be released from the stent over an at least a several week period, typically 4–8 weeks, and optionally over a 2–3-month period or more. Two methods for loading the drug on a stent are discussed below.

a. Direct Surface Attachment

The drug is coated directly onto the stent by, for example, applying a solution of drug to the stent surface by dip coating, spray coating, brush coating, or dip/spin coating, and allowing the solvent to evaporate to leave a film of drug on the stent surface. In studies performed in support of the invention, a 42-O-alkoxyalkyl rapamycin derivative, 42-O-(2-ethoxyethyl) rapamycin, was applied directly to the surface of a metal stent from an ethyl acetate solution. The drug solution was painted on the stent surface and the solvent was removed by evaporation to leave a film of 42-O-(2-ethoxyethyl) rapamycin on the stent. The drug film was sufficiently adherent to permit catheter implantation of the stents into pigs and retention of the drug on the stent surface for release. A membrane can be optionally applied over the drug film to change the drug release characteristic. Polymer membranes can be formed by dip coating or spray coating, as is well known in the art. The membrane can also be applied to the stent surface by a vapor deposition process or a plasma polymerization process. In one exemplary embodiment, a polytetrafluoroethylene (Teflon®) or parylene film is formed by vapor deposition as is well known in the art, to modify the drug release rate from the stent. Other suitable polymers and nonpolymers for formation of diffusion controlling membranes include polyimides (via vapor deposition or by solvent coating), fluorinated polymers, silicones (vapor/plasma or deposition), polyketones (PEEK, etc.), polyether imides, vapor/plasma deposited polyacrylates, plasma polymerized polyethyleneoxide (PEO), and amorphous carbon.

The surface of the stent can be treated prior to application of the drug, to enhance adhesion of the drug and/or to increase surface area for retention of a higher drug load. In one embodiment, the stent surface is physically treated. Physical treatment of the surface can include roughening with sand paper or by sand or glass microbead blasting. Etching of the stent surface with a laser can also be done to alter the stent surface. Such physical treatment methods achieve an increased stent surface area, for example, by forming microscopic pores, undulations, pockets, grooves, or channels in the stent surface. This technique can also serve to enhance adhesion of drug to the stent surface.

In another embodiment the stent surface is chemically treated to create a rougher surface or an activated surface, both serving to enhance and increase drug retention. For example, a stent surface can undergo a process of passivation, where a heated nitric acid solution creates an oxide on the stent surface to promote adhesion and/or to prepare the surface for subsequent organosilane attachment. Stent surfaces can also be chemically activated to promote attachment of a drug.

It will be appreciated that application of the drug directly to the stent surface can be done for stent bodies formed of metal or polymer. Surface treatments prior to application of the drug are also suitable for both polymer-based and metal-based stent bodies. The treatment conditions can be tailored according to the material from which the stent is formed.

In another embodiment of the invention, the 42-O-alkoxyalkyl rapamycin derivative is applied to the stent resulting in a glassy layer. "Glassy" as used herein refers to the physical state of the material where the layer is visually transparent or translucent and is non-crystalline. A glassy layer of the derivative compounds described herein is achieved, for example, by applying to the stent surface a concentrated solution of a compound in an organic solvent. Removal of the solvent yields a film of drug, where the film has few or no crystalline drug domains. Such films having a thin profile may be applied to the stent surface before or after reduction in diameter (i.e. crimping) as required to mount the device on the delivery catheter.

In this embodiment where the drug is applied directly to the surface of the stent, it is additionally contemplated to apply over the drug layer a membrane that serves to control release of the drug, thereby controlling its bioavailability. A membrane prepared from any natural or synthetic compound is contemplated, with a preferred type of membrane composed of a polymer. A wide range of polymers can be selected according to the desired release of drug from the stent. The polymer can be pre-formed into a membrane that is placed over the drug-coated stent in the form of a sheath, or the polymer membrane can be formed directly over the drug layer by a process selected to disturb or disrupt the drug layer.

b. Polymer Coating

An alternative method of applying the drug to the stent is to incorporate the drug into a polymer film that is formed on the stent surface or is carried on the stent. Typically, a solution of polymer and drug in a solvent is prepared and then applied to the stent. The solution is applied to all or a portion of the stent surfaces. After solvent evaporation, a polymer film containing drug remains on the stent surface. A preferred coating method is described in co-owned U.S. application Ser. No. 10/133,814 and PCT application no. PCT/US03/12750, incorporated by reference herein. In this method, a drug-containing solution is applied directly to the stent surface by flowing the drug from a moveable pressurized column, where the motion of the column is computer controlled. It is also possible to apply the drug-containing solution via spraying.

Yet another method of applying the polymer/drug/solvent mixture to the stent include or brushing, dipping, or rolling the mixture on to the stent surface from a suitable applicator, such as a brush, dipping fixture, or petrie dish containing a thin liquid layer of the mixture.

Polymers for use in this embodiment may be any biocompatible polymer material from which entrapped compound can be released by diffusion and/or released by erosion of the polymer matrix. Two well-known non-erodable polymers for the coating substrate are polymethylmethacrylate and ethylene vinyl alcohol. Methods for preparing these polymers in a form suitable for application to a stent body are described for example, in US 2001/0027340A1 and WO00/145763, both documents incorporated herein by reference. Other non-erodable polymers suitable for use in the invention include polyacrylates and their copolymers (PMMA, PMMA/PEG copolymers, polyacrylamides, etc.), silicones (polydimethly siloxanes etc), fluorinated polymers (PTFE etc.), poly vinyl acetate, poly vinyl alcohol and its copolymers, polyolefins and copolymers (with e.g. styrene, etc.), nondegradable polyurethanes (e.g. urethanes containing siloxane or carbonate soft segments), polyamides, hydroxyapatite, phosphorylcholines, polysulfones, polyketones, polyvinypyrrolidone, polystyrene, and ABS, polyvinyls-chloride, halide, polycarbonate. Bioerodable polymers are also suitable for use, and exemplary polymers include poly-l-lactide, poly-dl-lactide polymers, and polyglycolic acid-polylactic acid co-polymers, polyglycolides (PGA, poly (lactide-co-glycolide), polycaprolactone, polydioxanone, polyanhydrides, polyorthoesters, polycyanoacrylates, polyphosphazenes, polyglutamates, polyhydroxybutyric acid (PHB), polyhydroxyvaleric acid (PHV), poly (PHB-co-PHV), polysaccharides (cellulose, dextran, chitin, etc.), proteins (fibrin, casein; etc.), natural polymers (gelatin, hyaluronans, etc.), poly(DTH iminocarbonate), polytrimethylene carbonate, polyethylene imine, tyrosines (pseudo amino acids), polyrotaxanes, acrylate-based polymers or copolymers (including hydrogels), polyphosphoesters, degradable polyurethanes, poly (ether-ester) copolymers (e.g. PEO and its copolymers with PBT, etc.), poly ester/ether amides, and polyalkylene oxalates. Depending on the polymer selected and the properties of the drug, the polymer may contain up to 80% by dry weight of the active compound distributed within the polymer substrate. Generally, the polymer film can contain between about 35–80% dry weight active compound and 20–65% percent by dry weight of the polymer.

The thickness of the drug-laden polymer film is typically between about 3 microns and 30 microns, depending on the nature of the polymer matrix material forming the coating and the relative amounts of polymer matrix and active compound. Ideally, the coating is made as thin as possible, e.g., 15 microns or less, to minimize the stent profile in the vessel at the injury site. The coating should also be relatively uniform in thickness across the upper (outer) surfaces, to promote even distribution of released drug at the target site. A cross-sectional view of a stent coated with a drug-polymer matrix is shown in FIG. 3C, where the stent tubular member 24 is coated with a drug-polymer layer 32. Here the external stent surface has a slightly thicker drug-polymer layer than the internal stent surface.

In another embodiment, a polymer underlayer is applied to the stent surface, prior to formation of the drug-laden polymer matrix. The purpose of the underlayer is to help bond the drug-laden polymer coating to the stent-body, that is, to help stabilize the coating on the surface of the stent. This is particularly valuable where a high percentage of the compound, e.g. between 35–80 weight percent compound, is present in the polymer matrix. Suitable polymer underlayers can be formed of poly(d, l-lactic acid), poly(l-lactic acid), poly(d-lactic acid), ethylene vinyl alcohol (EVOH), ε-caprolactone, ethylvinyl hydroxylated acetate (EVA), polyvinyl alcohol (PVA), polyethylene oxides (PEO), paryLAST™, parylene (poly(dichloro-para-xylylene)), silicone, polytetrafluoroethylene (TEFLON™) and other fluoropolymers, and co-polymers thereof and mixtures thereof. The underlayer can be deposited from a solvent-based solution, by plasma-coating, or by other coating or deposition processes (see, for example, U.S. Pat. No. 6,299,604). The underlayer may have a typical thickness between 1–5 microns.

Based on the foregoing, the various configurations of stents contemplated for use as a carrier for a 42-O-alkoxyalkyl rapamycin derivative can be appreciated. Stents formed of a metal that carry the drug directly on the metallic surface or in a polymer film applied to the metal surface directly or in combination with a polymer underlayer are contemplated. Stents formed of a polymer, biodegradable or non-biodegradable, that carry the drug directly on or in the stent surface or in a polymer film applied to the stent surface directly or in combination with a polymer underlayer are also contemplated. Thus, it is also within the scope of the present invention to produce a completely bioerodable stent by forming the stent body of a bioerodable polymer and the drug-laden polymer matrix of a bioerodable polymer.

Also contemplated is the use of a second bioactive agent effective for treating the disease or disorder of concern or to treat any anticipated secondary conditions that might arise. For example, if the 42-O-alkoxyalkyl rapamycin derivative is administered for treatment of restenosis, a second compound to minimize blood-related events, such as clotting or thrombosis, that may be stimulated by the original vascular injury or the presence of the stent, or to improve vascular healing at the injury site can be included. Exemplary second agents include anti-platelet, fibrinolytic, or thrombolytic agents in soluble crystalline form or nitric-oxide (NO) donors which stimulate endothelial cell healing and control smooth muscle cell growth. Exemplary anti-platelet, fibrinolytic, or thrombolytic agents are heparin, aspirin, hirudin, ticlopidine, eptifibatide, urokinase, streptokinase, tissue plasminogen activator (TPA), or mixtures thereof. If the 42-O-alkoxyalkyl rapamycin derivative is intended for use as an anti-neoplastic agent, a second agent commonly used for chemotherapy of neoplastic diseases can be included. Exemplary second chemotherapeutic agents include paclitaxel, platinum compounds, cytarabine, 5-fluorouracil, teniposide, etoposide, methotrexate, doxorubicin, and the like. The amount of second-agent included in the stent coating will be determined by the period over which the agent will need to provide therapeutic benefit. The second agent may be included in the coating formulation that is applied to the stent-body or may be applied directly to the stent surface.

IV. Methods of Use

The 42-O-alkoxyalkyl rapamycin-derivative compounds are intended for use in treating any condition responsive to rapamycin, everolimus, Abbott ABT 578, tacrolimus, paclitaxel, any of the class of compounds commonly known as macrocyclic trienes or macrocyclic lactones, and/or other anticancer agents. This includes any condition associated with wound healing, such as post-surgical procedures involving a vessel or an organ transplant procedure, neoplastic diseases, where, for example, the polymer composition is placed directly at a site of cancer, such as a solid tumor. Inflammation and infection are also conditions treatable with the 42-O-alkoxy-alkyl derivatives. The compounds can also be used for vascular treatment methods, and specifically for restenosis.

With respect to treatment of vascular injury or inflammation, the risk and/or extent of restenosis in a patient who has received localized vascular injury, or who is at risk of vascular occlusion, can be minimized using a composition comprising a 42-O-alkoxyalkyl rapamycin derivative compound. Typically the vascular injury is produced during an angiographic procedure to open a partially occluded vessel, such as a coronary or peripheral vascular artery, but may also be created by more chronic inflammatory conditions, such as atherosclerosis. In the angiographic procedure, a balloon catheter is placed at the treatment site, and a distal-end balloon is inflated and deflated one or more times to force the narrowed or occluded vessel open. This vessel expansion, particularly involving surface trauma at the vessel wall where plaque may be dislodged, often produces enough localized injury that the vessel responds over time by cell proliferation and reocclusion. Not surprisingly, the occurrence or severity of restenosis is often related to the extent of vessel stretching involved in the angiographic procedure. Particularly where overstretching is 35% or more, restenosis occurs with high frequency and often with substantial severity, often causing vascular occlusion.

In studies conducted in support of the invention, stents coated with 42-O-(2-ethoxyethyl) rapamycin were prepared and inserted with a catheter into test animals. The stent used in the studies was a commercially available "S-Stent™" that is a highly flexible, corrugated ring stent laser cut from a stainless steel hypotube. Each corrugated ring has a total of six serially connected, S-shaped segments. There are two bend joints within each S-shaped segment that allow the stent to expand during deployment. These bend joints have undercuts that increase flexibility and reduce the expansion forces required while deploying the stent and obtaining good vessel wall apposition.

Successive rings in the stent are connected by two short links, with the successive pairs of these links oriented in 90 degree quadrature around the circumference of successive rings (QUADRATURE LINKS™). The links are believed to increase the longitudinal flexibility of the stent, while maintaining high hoop strength. Importantly, the mechanical design of the stent combines a repeating "S" symmetry and very short segment lengths to provide remarkable flexibility and high vessel wall support in both straight and curved vessels. The flexibility of the S-Stent allows it to be easily placed into tortuous coronary vessels, and enhances conformability with the blood vessel after implantation.

The S-Stent was specifically designed with a uniform and repeating pattern in order to achieve the objective of uniform drug distribution in the vessel wall as drug is released from the stent struts. The expansion characteristics of the stent insure that minimum stresses are applied to the coating during expansion, as a further attempt to eliminate tearing or cracking of the coating during deployment.

The stent has moderate radiopacity that is sufficient for locating the stent in most vessels during deployment when using a high resolution angiography system. The sizes of stents range from 4 mm to 60 mm in length, from 1 mm to 12 mm in diameter when fully expanded and are provided premounted on a catheter delivery system that employs an expandable polymeric balloon. The working length of the delivery catheter is approximately 142 cm and has a shaft diameter of 2.9 French. This catheter will accept a 0.014" guide wire. The working length of the delivery balloon is as required to match the length of the stent. There are radiopaque marker bands on the delivery catheter that are located under the shoulders of the balloon to aid in the placement of the stent.

S-stents were prepared as described in Example 4 by preparing a solution of 42-O-(2-ethoxyethyl) rapamycin and poly-1-lactic acid polymer in acetone. The drug-polymer solution was applied to the external surface of the stent using a microprocessor-controlled syringe pump to precision dispense the solution. This method of applying a solution to a stent is described in co-owned PCT application number PCT/US03/12750, the disclosure of which is incorporated by reference herein.

The in vitro release rate of drug from the stents into an unstirred, ethanol-water bath at 37° C. was measured and the results are shown in FIG. 4. The six curves in FIG. 4 correspond to six stents carrying a poly-dl-lactic acid polymer loaded with 42-O-(2-ethoxyethyl) rapamycin. Each stent held between about 224–235 µg of drug, with an average drug load of 230 µg. The polymer-drug coated stents were sterilized at 25 KGy or at 27.5 KGy prior to measuring the release rate. The elution curves show the controlled release of drug from the polymer layer carried on the stent, with less than half of the drug load released into the bath at 96 hours.

After preparation of the stents having a polymer-drug coating, they were implanted, as described in Example 5, into pigs for a thirty day period. The swine model was chosen as the experimental species for this study since the size of the heart and great vessels allows for a technically feasible device evaluation. Additionally, the size of the pig coronary artery is comparable to humans and allows for usage of standard clinical devices. Also, the pig is an excellent model for coronary vascular evaluations and therapy models and is close to human vascular responses in many ways. Also, the relative size of the animals allows accurate visualization using standard angiographic equipment. Swine are the most appropriate large animal model for restenosis, as they most closely resemble human vascular reactivity (Gravanis et. al., JACC, April 1993).

As described in Example 5, nine stents eluting 42-O-(2-ethoxyethyl) rapamycin from a polymer layer of poly-lactic acid were implanted in pigs and six control, bare metal stents were implanted. As comparative controls, 18 stents eluting everolimus and 12 stents eluting 42-O-hydroxy heptyl rapamycin were implanted. Quantitative coronary angiography was performed to measure the vessel lumen diameter immediately before and after stent placement and also 30 days later just prior to the follow-up angiogram taken at animal sacrifice. (Bell et al., *Cathet. Cardiovasc. Diagn.*, 40:66–74 (1997)). Percent stenosis (% stenosis) was determined from the measurements as:

$$\% \text{ Stenosis} = [(RVD - MLD)/RVD] \times 100$$

where MLD is minimum lumen diameter and RVD is distal and proximal reference vessel diameter. The stent to artery ratio was also calculated from these measurements. The angiographic percent stenosis was calculated from the measurements of minimum lumen diameter obtained at the follow-up angiogram.

As described in Example 5, after the 30 day study period, the stented vessels segments were processed for routine histology, sectioned, and stained. FIGS. 5 and 6 show exemplary results from the study. FIGS. 5A–5I are computer-generated photomicrographs of histology slides for a pig implanted with three 42-O-(2-ethoxyethyl) rapamycin eluting stents, the stents placed in the left anterior descending artery (FIGS. 5A–5C), the left circumflex artery (FIGS. 5D–5F), and the right coronary artery (FIGS. 5G–5I). FIGS. 5A, 5D, and 5G are views showing the stent in place in the vessel. FIGS. 5B, 5E, and 5H are cross-sectional views of the vessel, with the stent struts in cross-sectional view visible. FIGS. 5C, 5F, and 5I show the vessel-cross section at a higher magnification, with the neoinitmal response, or lack thereof, visible.

Figure 6A:
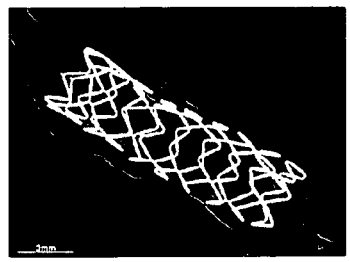
FIGS. 6A–6I are computer-generated photomicrographs of histology slides for a pig implanted with three 42-O-(2-ethoxyethyl) rapamycin eluting stents, the stents placed in the left anterior descending artery (FIGS. 6A–6C), the left circumflex artery (FIGS. 6D–6F), and the right coronary artery (FIGS. 6G–6I)
Figure 6B:
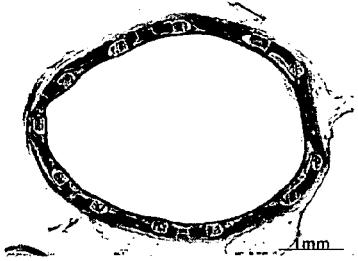
Figure 6C:
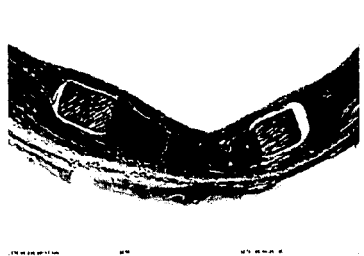
Figure 6D:
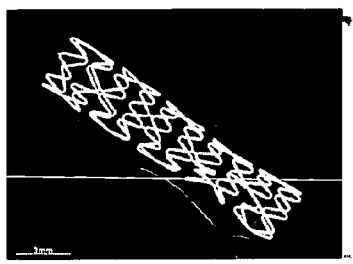
Figure 6E:
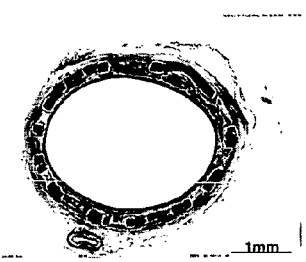
Figure 6F:
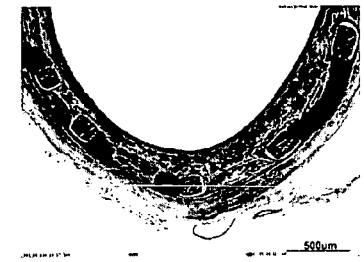
Figure 6G:
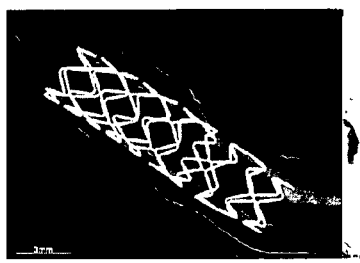
Figure 6H:
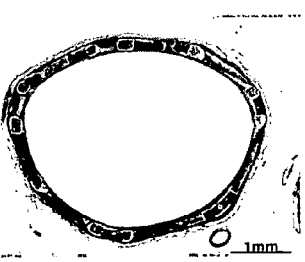
Figure 6I:
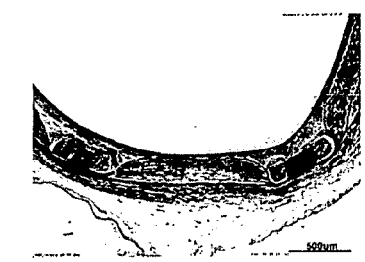

FIGS. 6A–6I are computer-generated photomicrographs of histology slides for a second exemplary pig implanted with three 42-O-(2-ethoxyethyl) rapamycin eluting stents, the stents placed in the left anterior descending artery (FIGS. 6A–6C), the left circumflex artery (FIGS. 6D–6F), and the right coronary artery (FIGS. 6G–6I). FIGS. 6A, 6D, and 6G are views showing the stent in place in the vessel. FIGS. 6B, 6E, and 6H are cross-sectional views of the vessel, with the stent struts in cross-sectional view visible. FIGS. 6C, 6F, and 6I show the vessel-cross section at a higher magnification, with the neoinitmal response, or lack thereof, visible.

FIGS. 7–9 correspond to photomicrographs for control, bare metal stents placed in vessels for 30 days. FIGS. 7A–7C show the right coronary artery of a control animal 30 days after implant of a bare, metal stent, where FIG. 7A shows an image of the stent in place in the artery and FIGS. 7B–7C show cross-sectional views of the stent at two different magnifications.

FIGS. 8A–8C show the left anterior descending artery of a control animal 30 days after implant of a bare, metal stent, where FIG. 8A shows an image of the stent in place in the artery and FIGS. 8B–8C show cross-sectional views of the stent at two different magnifications.

FIGS. 9A–9C show the left circumflex artery of a control animal 30 days after implant of a bare, metal stent, where FIG. 9A shows an image of the stent in place in the artery and FIGS. 9B–9C show cross-sectional views of the stent at two different magnifications.

The photographs in FIGS. 5–9 permit determination via planimetry of the area of new tissue inside the stent after 30 days in vivo. The average thickness of new tissue formed inside the stent for each implant was determined and plotted against an injury score, also determined after the 30 day test period. A least-squares linear regression analysis of the data provides a sensitive method to compare the therapeutic benefit of different stent compositions.

The degree of vascular injury was also quantified by assigning an "injury score" based on the amount and length of tear of the different wall structures. The degree of injury was calculated as follows:

0=intact internal elastic lamina
1=ruptured internal elastic lamina with exposure to superficial medial layers (minor injury)
2=ruptured internal elastic lamina with exposure to deeper medial layers (medial dissection)
3=ruptured external elastic lamina with exposure to the adventitia.

The mean injury score for each arterial segment was calculated by dividing the sum of injury scores at each stent strut site by the total number of stent struts in the proximal, middle, and distal stent sections using the method described by Schwartz et al. (*J. Am. Coll. Cardiol.*, 19:267–274 (1992)).

Figure 10:
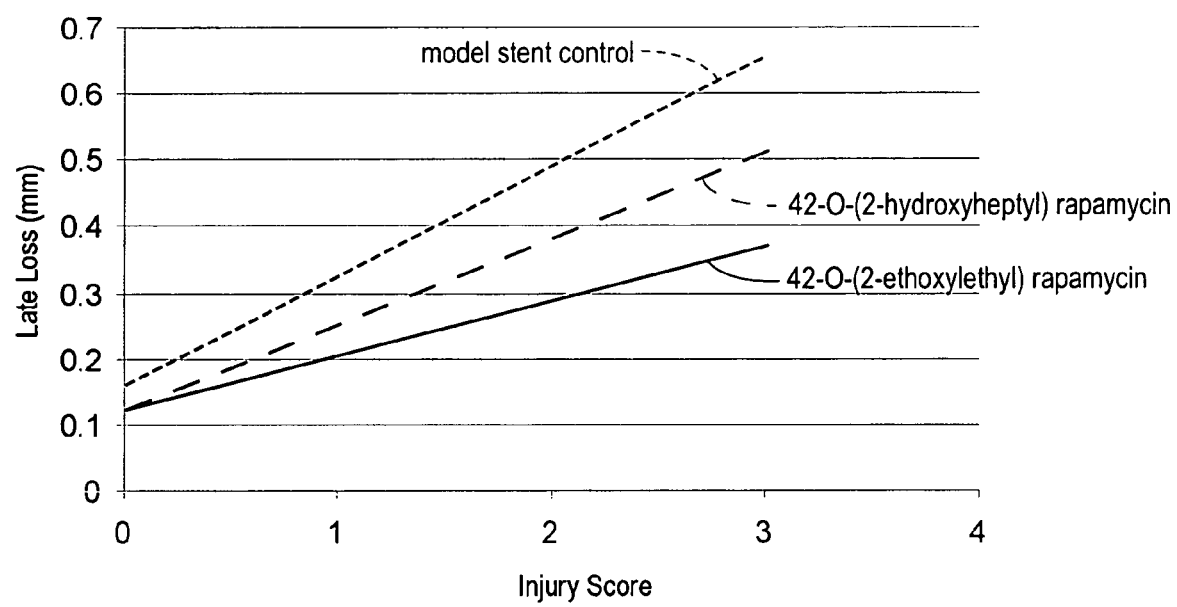
FIG. 10 is a plot of late loss, in mm, as a function of injury score for 42-O-(2-ethoxyethyl) rapamycin eluting stents (solid line), 42-O-hydroxy heptyl rapamycin eluting stents (dashed line), and control (bare metal) stents (dotted line), 30 days after implantation in pig vessels.

After analysis of the late loss and injury scores, the average late loss as a function of injury score was plotted for the test stents in each animal. FIG. 10 shows a plot of late loss, in mm, as a function of injury score for 42-O-(2-ethoxyethyl) rapamycin eluting stents (solid line), 42-O-hydroxy heptyl rapamycin eluting stents (dashed line), and control (bare metal) stents (dotted line). The stents were in place in the vessel for 30 days. Stents eluting 42-O-(2-ethoxyethyl) rapamycin showed a neointimal response to injury of 0.83 mm/injury score increment (i.e., slope of the regression line) and an intercept of the zero injury of 0.126 mm. Stents eluting 42-O-hydroxy heptyl rapamycin had a neointimal response to injury of 0.126 mm/injury score increment (i.e., slope of the regression line) and an intercept of the zero injury of 0.130 mm. The bare metal stents showed a neointimal response to injury of 0.165 mm/injury score increment (i.e., slope of the regression line) and an intercept of the zero injury of 0.165 mm. Thus, stents eluting 42-O-(2-ethoxyethyl) rapamycin had a lower neointimal thickness at 30 days (i.e. late loss) than stents eluting 42-O-hydroxy heptyl rapamycin or than the control metal stents.

Figure 11:
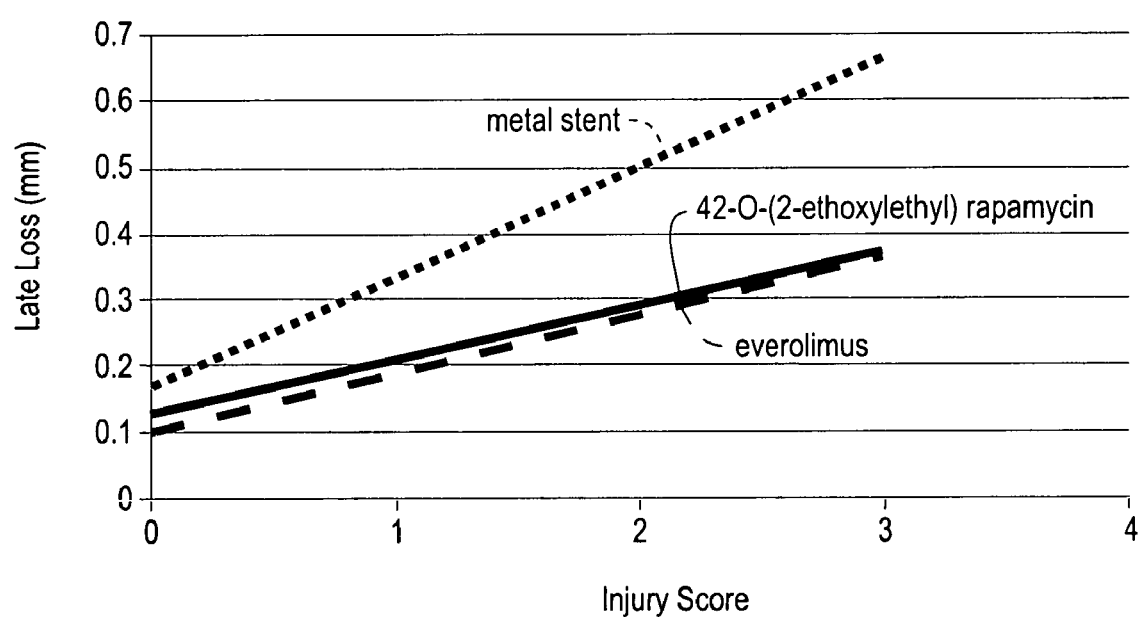
FIG. 11 is a plot of late loss, in mm, as a function of injury score for 42-O-(2-ethoxyethyl rapamycin eluting stents (solid line), 42-O-hydroxy heptyl rapamycin (i.e. everolimus)-eluting stents (dashed line), and control (bare metal) stents (dotted line), 30 days after implantation in pig vessels.

FIG. 11 is a similar plot, showing average late loss, in mm, as a function of injury score for 42-O-(2-ethoxyethyl) rapamycin eluting stents (solid line); everolimus-eluting stents (dashed line), and control (bare metal) stents (dotted line), 30 days after implantation in pig vessels. Again, it is apparent that stents eluting 42-O-(2-ethoxyethyl) rapamycin offer a therapeutic effect when compared to bare, metal stents.

In another study, stents carrying 42-O-(2-ethoxyethyl) rapamycin in the form of a polymer (poly-dl-lactic acid) coating were prepared for insertion into pigs with a vessel overstretch injury to the coronary artery. Comparative and control stents includes bare metal stents, stents having a polymer coating of poly-dl-lactic acid absent drug, stents carrying rapamycin in a poly-dl-lactic acid polymer coating, and stents carrying everolimus in a poly-dl-lactic acid polymer coating. The stents were inserted into vessels which seriously injured (averaging approximately 36% overstretch injury of the vessel) using an angioplasty balloon. The controlled overstretching using the balloon catheter caused severe tearing and stretching of the vessel's intimal and medial layers, resulting in exuberant restenosis at 28 days post implant. In this way, it was possible to assess the relative effectiveness of the various test compounds presented to the vessels on the same metal stent/polymer platform. At the time of insertion, the extent of overstretch was recorded as a percent balloon/artery (B/A) ratio.

TABLE 1

| Test Group | Stent length (mm) | Drug load (μg) | Polymer coat (μg) | B/A ratio (%) | Mean lumen loss (mm) | Neointimal area (mm$^2$) | Average Injury score[1] | Diameter stenosis[2] % |
|---|---|---|---|---|---|---|---|---|
| bare stent | | | | | | | | |
| 28 days | 18.7 | — | — | 1.33 | 1.69 | 5.89 | 1.9 | 72.0 |
| 6 months | 18.7 | — | — | 1.19 | 0.40 | 2.68 | 1.26 | 32.7 |
| polymer-coated stent | 18.7 | — | 1300 | 1.36 | 2.10 | 5.82 | 2.11 | 70.0 |
| rapamycin - high dose | 18.7 | 325 | 1300 | 1.39 | 1.07 | 3.75 | 2.10 | 55.0 |
| rapamycin - low dose | 18.7 | 180 | 1300 | 1.42 | 0.99 | 2.80 | 1.90 | 43.0 |
| everolimus - high dose | | | | | | | | |
| 28 days | 18.7 | 325 | 1300 | 1.37 | 0.84 | 3.54 | 1.89 | 38.0 |
| 6 months | 18.7 | 325 | 1300 | 1.31 | 1.15 | 4.18 | 2.67 | 68.5 |
| everolimus - low dose | 18.7 | 180 | 1300 | 1.36 | 1.54 | 3.41 | 2.10 | 53.0 |
| everolimus - med. dose | 18.7 | 275 | 640–780[3] | 1.36 | 0.85 | 2.97 | 2.13 | 45.0 |
| 42-O-(ethoxyethyl) rapamycin | 15 | 225 | 225 | 1.19 | 0.62 | 1.30 | 1.29 | 14.8 |

[1] injury scores quantify the degree of vascular injury based on the amount, length, and depth of tear and is scored using the scale of 1, 2, 3, given above.
[2] a lower score indicates higher efficacy
[3] 26% drug to polymer ratio The data in Table 2 shows that while the drug-carrying stents performed better than the bare metal stent or the polymer-coated stent, the stent carrying 42-O-(2-ethoxyethyl) rapamycin resulted in the lowest mean lumen late loss and percent diameter stenosis. Thus 42-O-(2-ethoxyethyl) rapamycin demonstrated superiority for suppression of cell proliferation when directly compared to rapamycin and other known rapamycin derivatives in the pig coronary artery overstretch injury model.

From the foregoing, it can be appreciated how various feature and objects of the invention are achieved. 42-O-alkoxyalkyl derivatives of rapamycin, as exemplified by 42-O-(2-ethoxyethyl) rapamycin, have in vitro potency similar to or greater than the potency of rapamycin and of another rapamycin derivative, 42-O-hydroxy heptyl rapamycin. The in vivo activity of 42-O-alkoxyalkyl rapamycin derivatives was illustrated using stents coated with the drug and placed in the vessel of an animal for inhibition of restenosis. The 42-O-alkoxyalkyl rapamycin derivatives can be formulated into preparations suitable for topical, parenteral, and local administration for use in treating any condition responsive to rapamycin, everolimus cancer agents, or other macrocyclic lactones.

V. EXAMPLES

The following examples further illustrate the invention described herein and are in no way intended to limit the scope of the invention.

Example 1

Preparation of 42-O-(2-ethoxylethyl) rapamycin (Biolimus A9)

A. Synthesis of 2-ethoxyethanol Triflate

To a stirred, cooled (0° C.) solution of 4.28 g 2-ethoxyethanol (Aldrich Chemical) and 10.14 g 2,6-lutidine in 160 mL $CH_2Cl_2$ under nitrogen was slowly added 19.74 g trifluoromethanesulfonic (triflic) anhydride. The mixture was washed with four portions of 200 mL brine and the organic solution dried over anhydrous sodium sulfate, filtered and concentrated. The residue was purified by flash chromatography on silica gel, 200400 mesh (75:25 hexanes-ethyl ether (v/v)) to afford the triflate of 2-ethoxyethanol: light yellow liquid, TLC $R_f$=0.47 using hexanes-ethyl ether 75:25 (v/v).

B. Reaction of 2-ethoxyethanol Triflate with Rapamycin

To a stirred solution of 1 g rapamycin, and 7.66 g 2,6-lutidine in 14.65 mL toluene held at 60° C. was added 5.81 g 2-ethoxyethanol triflate. Stirring was continued for 90 minutes after which 50 mL ethyl acetate was added to the reaction and the solution was washed with 50 mL 1M HCl. The organic material was washed with D.I. water until pH of wash solution was neutral and the organic solution was dried over anhydrous sodium sulfate, filtered, and concentrated. The residue was purified by flash chromatography on silica gel, 200–400 mesh (40:60 hexane-ethyl acetate (v/v) to give 210 mg 42-O-(2-ethoxyethyl) rapamycin. TLC $R_f$=0.41 using 40:60 hexane-ethyl acetate (v/v). MS (ESI) m/z 1008.5 $C_{55}H_{87}NNaO_{14}$. A mass spectrum of the title compound is shown in FIG. 1.

The chemical structure of 42-O-(2-ethoxyethyl) rapamycin was further verified by mass spectrometric tandem quadrupole experiments (CAD experiments, collisionally activated dissociation). These studies were done on a Thermo Finnigan, LCQ Advantage quadrupole ion trap mass spectrometer equipped with an electrospray ionization source. Direct infusion of the sample in methanol was done at a flow rate of 2.5 µL/min from a syringe. CAD experiments were carried out after obtaining maximum signal intensity. Helium was used as the collision gas. Collision energy was tuned during the MS/MS experiments to obtain the full range of fragments. The fragmentation patterns indicated the presence of the ion pair 1008.5→417.5. These results are consistent with the chemical structure of 42-O-(2-ethoxyethyl) rapamycin given above.

Purity of the product was determined by HPLC. A Zorbax SB-C18 HPCL system was used, with a 4.6 mm ID×250 mm (5 µm) column. A step gradient solvent system was utilized consisting of 100% (10% methanol-water), one minute; 50% (10% methanol-water)/50% methanol, one minute; 25% (10% methanol-water)/75% methanol, one minute; 100% methanol. A flow rate of 1.0 mL was used. Column temperature was 55° C. 2.0 µg of 42-O-(2-ethoxyethyl) rapamycin was injected onto the column in a volume of 20 µL methanol. Detection by UV at 278 nm. Purity was 98.7% (average of three runs; SD=0.2).

Example 2

Preparation of 42-O-(2-methoxyethyl) Rapamycin

A. Synthesis of 2-methoxyethanol Triflate

To a stirred, cooled (0° C.) solution of 1.80 g 2-methoxyethanol (Aldrich Chemical) and 5.07 g 2,6-lutidine in 80 mL CH2CL2 under nitrogen was slowly added 9.87 g trifluoromethanesulfonic (triflic) anhydride. The mixture was washed with five portions of 100 mL brine and the organic solution dried over anhydrous sodium sulfate, filtered and concentrated. The residue was purified by flash column chromatography on silica gel 200–400 mesh (75:25 hexane-ethyl ether (v/v)) to afford the triflate of 2-methoxyethanol: light brown liquid, TLC=0.61 using the same solvent system as above.

B. Reaction of 2-methoxyethanol Triflate with Rapamycin

A mixture of 8.0 mg rapamycin, 52.9 µL lutidine, and 34 µL 2-methoxyethanol triflate was held at 60° C. in a 1.5 mL microcentrifuge tube (Laboratory Plastics) for 1.5 hours. 150 µL ethyl acetate and 150 µL 1M HCl was added and the solutions mixed by vigorous shaking. Separation and direct preparative TLC of the organic layer (40:60 hexanes/ethyl acetate (v/v)) resulted in 2.3 mg 42-O-(2-methoxy ethyl) rapamycin. MS (ESI) M/Z 994.6 $C_{54}H_{85}NNaO_{14}$. MS/MS 995→403.

Example 3

In Vitro Potency of 42-O-(2-ethoxyethyl) Rapamycin Derivative

Smooth muscle cell cultures were subjected to increasing doses of 42-O-(2-ethoxyethyl) rapamycin, 42-O-(hydroxy heptyl) rapamycin, and rapamycin over 8 or 9 orders of magnitude concentration in the culture medium. The ability of the cell culture to reproduce was assessed after drug exposure by addition of a colored reagent which causes a color change in the surviving cells, followed by cell cytometry. The ability of the cells to migrate was assessed when cells from the culture moved through a porous membrane barrier adjacent the culture, and again by staining and cell cytometry. The results of these tests are shown in FIG. 2 for human smooth muscle cells. The results show that the 42-O-(2-ethoxyethyl) rapamycin (squares) and 42-O-(hydroxy heptyl) rapamycin (diamonds) have similar potency in growth suppression of smooth muscle cells over 5 orders of magnitude concentration, for both porcine and human cells.

Example 4

Preparation of Stents Containing 42-O-(2-ethoxyethyl) Rapamycin 100 mg poly (dl-lactide) was dissolved into 2 mL acetone at room temperature. 5 mg 42-O-(2-ethoxyethyl) rapamycin was placed in a vial and 100 μL lactide solution added. A microprocessor-controlled syringe pump was used to precision dispense 4.5 μL of the drug containing poly-dl-lactide solution to the outer surface of a metal S-Stent (available from Biosensors International Inc, Newport Beach, Calif.). Evaporation of the solvent resulted in a uniform, drug containing single polymer layer on the stent.

Comparative stents containing everolimus or 42-O-hydroxy heptyl rapamycin were prepared identically.

Example 5

In vivo Testing of Stents Carrying 42-O-(2-ethoxyethyl) Rapamycin

A. Animal Model

Six out-bred juvenile swine weighing between 30–40 kg were obtained. The animals were housed and quarantined for a minimum of three days prior to entering into the study. All animals were examined and housed in facility-approved pens under sanitary conditions. A nutritionally balanced, standard pig chow was fed to the study animals, and water was provided ad libitum.

B. Stent Placement

Three days prior to insertion of stents each animal received 650 mg aspirin, 500 mg ticlopidine daily, and 120 mg verapamil daily. Aspirin (325 mg) daily was given throughout the duration of the study. The animals were fasted twelve hours prior to stent placement.

For stent placement, each animal was immobilized with an intramuscular injection of 0.5 mg/kg acepromazine, 20 mg/kg ketamine, and 0.05 mg/kg atropine. An intravenous catheter was placed in an ear vein, and anesthesia was induced with 5–8 mg/kg thiopental. The animal was intubated and ventilated; anesthesia was maintained with inhaled 1–2% isoflurane. A loading dose of intravenous bretylium tosylate (10 mg/kg) was administered for anti-arrhythmic therapy.

The surgical site was shaved, cleaned, and draped. An incision was made for blunt dissection of the tissue place above the access artery (either the right and/or left carotid artery or the right and/or left femoral artery). The distal and proximal segments of the artery were secured with suture; the distal vessel was ligated. An arteriotomy was performed and an introducer sheath placed in the artery.

A guiding catheter was placed into the sheath and advanced under fluoroscopic guidance into the coronary arteries. After placement of the guide catheter, angiographic images of the vessel were obtained to identify a suitable location for stent deployment. The tip of the guiding catheter was included in the captured images to facilitate quantitative coronary angiography (QCA) measurements. A 0.014" guide wire was used to deliver stents to pre-determined sites selected from the left anterior descending (LAD), left circumflex (LCX), and/or right coronary (RCA) arteries. Stents were typically placed in up to three coronary arteries, with only one stent placed in any one artery. When needed, additional balloon inflations were made to assure positive apposition of the stent against the vessel wall. The final stent diameter was selected to create an "overstretch injury" of 20%±10% over mean vessel diameter (MLD). Following stent deployment, additional angiographic images of the treated vessel segments were obtained in the same orientation as the initial images.

Intravenous bretylium tosylate (10 mg/kg) was administered at the end of the procedure for anti-arrhythmic therapy. Following the procedure, the catheters were removed, the proximal vessel ligated with O-silk, and the arterial cutdown site repaired in a three-layer fashion. The facia and subcutaneous layers were closed with a running suture using 2-0 monocryl. The animal was allowed to recover.

Nine stents eluting 42-O-(2-ethoxyethyl) rapamycin from a polymer layer of poly-lactic acid were implanted in pigs and six control, bare metal stents were implanted. As comparative controls, 18 stents eluting everolimus and 12 stents eluting 42-O-hydroxy heptyl rapamycin were implanted. The results are shown in FIGS. 5–9.

C. Monitoring of Test Animals

At the end of the study, the animals were euthanized and a thoracotomy was performed. The coronary arteries were perfused with at least one liter of formalin infused into the coronary arteries. A cardiectomy was then performed and the vessels were visually inspected for any external or internal trauma. The stented vessels were removed from the heart, stored in sealed laboratory bottles of new 10% formaldehyde solution, and packaged for histology preparation.

Quantitative angiography was performed to measure the vessel diameter immediately before and after stent placement and also at follow-up (i.e. animal sacrifice). The stent to artery (i.e. B/A or Balloon/Artery) ratio was calculated from these measurements. The angiographic percent stenosis was calculated from the measurements of minimum lumen diameter obtained at the follow-up angiogram. Histologic measurements were made from sections from the native vessel proximal and distal to the stents as well as the proximal, middle, and distal portions of the stents. The mean injury score for each arterial segment was calculated by dividing the sum of injury scores at each stent strut site by the total number of stent struts in the proximal, middle, and distal stent sections using the method described by Schwartz et al. (J. Am. Coll. Cardiol., 19:267–274 (1992)).

Neointimal thickness was measured at the native vessel proximal and distal to the stents and at the proximal, middle, and distal portions within the stents. The neointima, media, and total vessel cross sectional areas of each mid-stent section were measured with digital histomorphometry to determine the neointimal area and percent area stenosis defined as [(intimal area/native lumen area)×100]; where the native lumen area is the area delineated by the internal elastic lamina. Data were expressed as the mean±standard deviation and as the maximum percent cross sectional area narrowing for each specimen. Statistical analysis of the histologic and angiographic data were accomplished using analysis of variance (ANOVA). A $p<0.05$ was considered statistically significant.

QCA measurements were made according to the teaching of Bell et al. (Cathet. Cardiovasc. Diagn., 40:66–74 (1997)). Percent stenosis (% stenosis) was determined by:

$$\% \text{ Stenosis} = [(RVD-MLD)/RVD] \times 100$$

where MLD is minimum lumen diameter and RVD is distal and proximal reference vessel diameter.

Histomorphometric analysis included lumen cross sectional area, internal elastic lamina (IEL) and/or stent area, neointimal area, medial area, adventitial area, percent in-stent stenosis, intimal thickness at each stent strut, and injury score at each stent strut.

The degree of vascular injury was also quantified by assigning an "injury score" based on the amount and length of tear of the different wall structures. The degree of injury was calculated as follows:
0=intact internal elastic lamina
1=ruptured internal elastic lamina with exposure to superficial medial layers (minor injury)
2=ruptured internal elastic lamina with exposure to deeper medial layers (medial dissection)
3=ruptured external elastic lamina with exposure to the adventitia.

The mean injury score for each arterial segment was calculated by dividing the sum of injury scores at each stent strut site by the total number of stent struts in the proximal, middle, and distal stent sections using the method described by Schwartz et al. (J. Am. Coll. Cardiol., 19:267–274 (1992)).

D. Histology

The stented segments were processed for routine histology, sectioned, and stained following standard histology lab protocols as described by Isner et. al (*Biochemical and Biophysical Research Communications*, 235:311–316 (1997)). Hematoxylin and eosin stain, elastic and connective tissue stain were performed in alternate fashion on serial sections through the length of the stent (distal/proximal reference vessel proximal/middle/distal stent).

Photographs of histology slides for animals treated with 42-O-(2-ethoxyethyl) rapamycin eluting stents are shown in FIGS. 5A–5I for one test animal having three stents placed in the left anterior descending artery (FIGS. 5A–5C), the left circumflex artery (FIGS. 5D–5F), and the right coronary artery (FIGS. 5G–5I); and in FIGS. 6A–6I for a second test animal having three stents placed in the left anterior descending artery (FIGS. 6A–6C), the left circumflex artery (FIGS. 6D–6F), and the right coronary artery (FIGS. 6G–6I).

Photographs of histology slides of vessels taken from six control animals having an implanted bare metal stent for 30 days are shown in FIGS. 7–9.

Although the invention has been described with respect to particular embodiments, it will be apparent to those skilled in the art that various changes and modifications can be made without departing from the invention.

The invention claimed is:

1. A compound of the form:

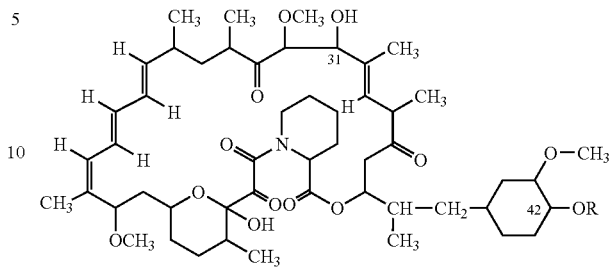

wherein R is —(CH$_2$)$_2$—O—CH$_2$CH$_3$.

2. A pharmaceutical composition comprising a compound according to claim 1 together with a carrier.

3. The composition according to claim 2, wherein said carrier is a pharmaceutical preparation having the form of an ointment or a gel.

4. The composition according to claim 2, wherein said carrier is comprised of polymer microparticles.

5. The composition according to claim 2, wherein said carrier is a pharmaceutical preparation having the form of a liquid, tablet, or suppository.

6. The composition according to claim 2 wherein said carrier is a stent.

7. The composition according to claim 6 wherein said stent is formed of metal or polymer.

8. The composition according to claim 7 wherein said stent is formed of a biodegradable polymer.

9. The composition according to claim 7, wherein said stent is metal and said compound is carried directly on the surface of the stent.

10. The composition according to claim 7, where said compound is carried in a polymer layer in contact with said stent.

11. The composition according to claim 8, where said compound is carried in a polymer layer in contact with said stent.

12. A method of treating any of the following conditions:
(i) restenosis;
(ii) wound healing;
(iii) vascular injury;
(iv) vascular inflammation; and
(v) transplant rejection, comprising administering a compound according to claim 1.

* * * * *

UNITED STATES PATENT AND TRADEMARK OFFICE
Certificate

Patent No. 7,220,755 B2                                                                                 Patented: May 22, 2007

On petition requesting issuance of a certificate for correction of inventorship pursuant to 35 U.S.C. 256, it has been found that the above identified patent, through error and without any deceptive intent, improperly sets forth the inventorship.
   Accordingly, it is hereby certified that the correct inventorship of this patent is: Ronald E. Betts, La Jolla, CA (US).

Signed and Sealed this Fourth Day of October 2011.

<div align="right">
ANDREW D. KOSAR<br>
<em>Supervisory Patent Examiner</em><br>
Art Unit 1621<br>
Technology Center 1600
</div>